(12) United States Patent
Nolan, Jr. et al.

(10) Patent No.: US 6,743,205 B2
(45) Date of Patent: Jun. 1, 2004

(54) INJECTOR SYSTEMS AND SYRINGE ADAPTERS FOR USE THEREWITH

(75) Inventors: William J. Nolan, Jr., Curtisville, PA (US); Michael A. Spohn, Butler, PA (US); John A. Haury, Sewickly, PA (US); Anthony S. McCoppin, Pittsburgh, PA (US); Frank A. Lazzaro, Pittsburgh, PA (US); Robert J. Ashcraft, Jr., Butler, PA (US); James Albert Dedig, Pittsburgh, PA (US); Christopher J. Blue, Pittsburgh, PA (US); David H. Berry, Pittsburgh, PA (US)

(73) Assignee: Medrad, Inc., Indianola, PA (US)

( * ) Notice: Subject to any disclaimer, the term of this patent is extended or adjusted under 35 U.S.C. 154(b) by 117 days.

(21) Appl. No.: 09/814,020

(22) Filed: Mar. 21, 2001

(65) Prior Publication Data

US 2001/0023336 A1 Sep. 20, 2001

Related U.S. Application Data

(63) Continuation of application No. 09/365,285, filed on Jul. 30, 1999, now abandoned.

(51) Int. Cl.[7] ............................................... A61M 37/00
(52) U.S. Cl. ....................................... 604/154; 604/131
(58) Field of Search ............................ 604/82, 131, 87, 604/218, 187, 154, 228, 227, 189, 68, 72, 181, 135, 232, 23, 140, 143; 128/DIG. 1, DIG. 12; 235/375, 462.01, 453; 222/386, 390, 327

(56) References Cited

U.S. PATENT DOCUMENTS

| 3,880,163 A | 4/1975 | Ritterskamp |
| 4,006,736 A | 2/1977 | Kransys et al. |
| 4,342,312 A | 8/1982 | Whitney et al. |

(List continued on next page.)

FOREIGN PATENT DOCUMENTS

| EP | 0 346 950 | 12/1989 |
| EP | 0 561 122 | 9/1993 |
| EP | 0 567 186 | 10/1993 |

(List continued on next page.)

OTHER PUBLICATIONS

Drawing of Dual Flange Injector Head (publicly disclosed in Jul. of 1995).

(List continued on next page.)

*Primary Examiner*—Michael J. Hayes
*Assistant Examiner*—Kevin C. Sirmons
(74) *Attorney, Agent, or Firm*—Gregory L. Bradley; Henry E. Bartony, Jr.

(57) ABSTRACT

An adapter includes a syringe carrier adapted to seat at least a portion of the syringe. The syringe carrier includes at least one rearward facing abutment member to abut at least one forward facing surface on a syringe. The syringe carrier includes an opening therein to allow a drive member of an injector to communicate forward force to the plunger through abutment without connective engagement between the drive member and the plunger. The adapter further includes a releasable mounting mechanism positioned to the rear of the syringe carrier to mount the adapter in a desired position relative to the front wall of the injector.

22 Claims, 36 Drawing Sheets

U.S. PATENT DOCUMENTS

| | | | |
|---|---|---|---|
| 4,465,473 A | | 8/1984 | Ruegg |
| 4,563,175 A | | 1/1986 | LaFond |
| 4,650,465 A | | 3/1987 | Langer et al. |
| 4,677,980 A | | 7/1987 | Reilly et al. |
| 4,695,271 A | | 9/1987 | Goethel |
| 4,978,335 A | | 12/1990 | Arthur, III |
| 5,269,762 A | | 12/1993 | Armbruster et al. |
| 5,279,569 A | | 1/1994 | Neer et al. |
| 5,300,031 A | | 4/1994 | Neer et al. |
| 5,322,511 A | | 6/1994 | Armbruster et al. |
| 5,383,858 A | | 1/1995 | Reilly et al. |
| 5,494,036 A | | 2/1996 | Uber, III et al. |
| 5,520,653 A | * | 5/1996 | Reilly et al. ............... 604/152 |
| 5,535,746 A | | 7/1996 | Hoover et al. |
| 5,662,612 A | | 9/1997 | Niehoff |
| 5,741,232 A | | 4/1998 | Reilly et al. |
| 5,779,675 A | * | 7/1998 | Reilly et al. ............... 604/131 |
| 5,795,333 A | | 8/1998 | Reilly et al. |
| 5,865,805 A | | 2/1999 | Ziemba |
| 5,913,844 A | | 6/1999 | Ziemba et al. |
| 5,944,694 A | | 8/1999 | Hitchins et al. |
| 5,947,929 A | | 9/1999 | Trull |
| 5,997,502 A | | 12/1999 | Reilly et al. |
| 6,080,136 A | | 6/2000 | Trull et al. |

FOREIGN PATENT DOCUMENTS

| | | |
|---|---|---|
| JP | 8-336592 | 12/1996 |
| JP | 9-122234 | 5/1997 |
| WO | WO 95/20410 | 8/1995 |
| WO | WO 95/26211 | 10/1995 |
| WO | WO 97/36635 | 9/1997 |
| WO | WO 99/10032 | 3/1999 |

OTHER PUBLICATIONS

Medrad MCT/MCT Plus Operation Manual, KMP 810P Revision B (1991), pp. 4–18 to 4–22 and 6–1 to 6–13.

Liebel Flarsheim Company, Angiomat 6000 Digital Injection System Operator's Manual, 600950 Rev. 1 (1990), pp. 3–6 to 3–8, 4–52 to 4–56.

Liebel–Flarsheim Company, Angiomat 6000 Contrast Delivery System Brochure (1992).

Liebel–Flarsheim Company, Angiomat CT Digital Injection System Operator's Manual 600964 (1990) pp. 1–3 to 1–4, 3–7 to 3–9, 4–37 to 4–39.

Liebel–Flarsheim Company, Angiomat CT Digital Injection System Operator's Manual 600964 Rev. A (1991) pp. 1–5, 3–12, 4–48 to 4–51.

Liebel–Flarsheim Company, CT 9000 ADV Digital Injection System Manual 800961–B, Feb. 1998, pp. 1–4 to 1–16.

International Search Report for Counterpart PCT Application No. PCT/US 00/20623.

* cited by examiner

US 6,743,205 B2

INJECTOR SYSTEMS AND SYRINGE ADAPTERS FOR USE THEREWITH

CROSS-REFERENCE TO RELATED APPLICATION

This application is a continuation of application Ser. No. 09/365,285, filed on Jul. 30, 1999 now abandoned, the contents of which are hereby incorporated by reference.

BACKGROUND OF THE INVENTION

The present invention relates to powered injector systems and syringe adapters for use therewith.

A number of injector-actuated syringes and powered injectors for use in medical procedures such as angiography, computed tomography, ultrasound and NMR/MRI have been developed. U.S. Pat. No. 4,006,736, for example, discloses an injector and syringe for injecting fluid into the vascular system of a human being or an animal. Typically, such injectors comprise drive members such as pistons that connect to a syringe plunger. For example, U.S. Pat. No. 4,677,980, the disclosure of which is incorporated herein by reference, discloses an angiographic injector and syringe wherein the drive member of the injector can be connected to, or disconnected from, the syringe plunger at any point along the travel path of the plunger via a releasable mechanism. A front-loading syringe and injector system is also disclosed in U.S. Pat. No. 5,383,858, the disclosure of which is incorporated herein by reference.

As discussed in U.S. Pat. No. 5,383,858, a syringe used with a front-loading injector preferably includes a readily releasable mounting mechanism for securing the syringe to the front wall of the injector. The use of specifically designed mounting mechanisms, however, prevents the use of syringes of other various types with front-loading injectors. Such syringes may, for example, include a syringe body, a plunger reciprocally mounted therein, and a plunger extension for transfer of force to the plunger.

U.S. Pat. No. 5,520,653, the disclosure of which is incorporated herein by reference, discloses several adapters designed to allow the use of various syringes with a front-loading injector. In one embodiment, the adapter of U.S. Pat. No. 5,520,653 includes a syringe carrier having a front end, a rear end, and syringe retaining channel located between the carrier front and rear ends for engaging at least a portion of the syringe flange. Mounting flanges near the rearward end of the carrier releasably mount the carrier in a desired position relative to the front wall of the injector. The adapter of U.S. Pat. No. 5,520,653 further includes a follower reciprocally mounted within the carrier. The follower has a front end that engages the syringe plunger extension when the syringe is installed in the carrier. A drive head opening in the carrier communicates with a pair of drive head slots positioned near the rear end of the follower for releasably mounting the follower in a desired position relative to the drive head of the injector.

Although U.S. Pat. No. 5,520,653 is a substantial improvement in the art, it remains desirable to develop improved adapters for use with syringes of various types to permit use of such syringes with front-loading injectors.

SUMMARY OF THE INVENTION

In general, the present invention provides an adapter for releasably mounting a syringe in a desired position relative to a front-loading powered injector. The syringe includes a body and a plunger slideably positioned within the body. The injector includes a front wall, an opening formed in the front wall, and a drive member reciprocally mounted in the injector. The adapter preferably includes generally a syringe carrier adapted to seat at least a portion of the syringe. The syringe carrier includes at least one rearward facing abutment member to abut at least one forward facing surface on the syringe. The syringe carrier includes an opening therein to allow the drive member of the injector to communicate forward force to the plunger through abutment without connective engagement between the drive member and the plunger. The adapter further includes a releasable mounting mechanism positioned to the rear of the syringe carrier to mount the adapter in a desired position relative to the front wall of the injector.

The syringe may further include a transition region over which the radius or width of the syringe decreases (for example, a generally frusto-conical region) attached to a forward end of the body. The abutment member may abut a forward facing surface created by the transition region. Preferably, the abutment member abuts the transition region only in the vicinity of the transition from the body to the generally frusto-conical region (for example, at to the outer edge of the transition region).

The syringe may further include a syringe flange attached to a rearward end of the body of the syringe. The abutment member may abut a forward facing surface of the syringe flange. Preferably, the abutment member abuts the syringe flange only in the vicinity of the transition from the body to the syringe flange.

In one embodiment, the adapter includes a first section and a second section rotatable relative to each other about a hinge axis generally perpendicular to a longitudinal axis of the adapter. The first section and the second section are preferably rotatable about the hinge axis to an open position to allow loading of the syringe into the adapter from a position to the rear of the hinge axis. The first section and the second section are also preferably rotatable about the hinge axis to a closed position to form the syringe carrier.

In another embodiment, the adapter includes a first section and a second section that are generally the same in construction. The first section and the second section are connectable to form the syringe carrier and the releasable mounting mechanism.

The present invention also provides an adapter for releasably mounting a syringe in a desired position relative to a powered injector. The syringe preferably includes a body and a plunger slideably position within the body as discussed above. The injector preferably includes a front wall, an opening formed in the front wall, and a drive member reciprocally mounted in the injector. The adapter includes a first section and a second section that are rotatable relative to each other about a hinge axis generally perpendicular to a longitudinal axis of the adapter to an open position to allow loading of the syringe into the adapter from a position to the rear of the hinge axis. The first section and the second section are also preferably rotatable about the hinge axis to a closed position to form a syringe carrier to seat at least a portion of the syringe.

The present invention also provides an adapter for releasably mounting a syringe in a desired position relative to a powered injector. The adapter preferably includes a first section and a second section that are of generally the same in construction. The first section and the section are connectable to form a syringe carrier to seat at least a portion of the syringe. Preferably, the first section and the section also form a releasable mounting mechanism positioned to the rear of the syringe carrier to mount the adapter in a desired position relative to the front wall of the injector.

BRIEF DESCRIPTION OF THE DRAWINGS

Other aspects of the invention and their advantages will be discerned from the following detailed description when read in connection with the accompanying drawings, in which.

DETAILED DESCRIPTION OF THE INVENTION

Figure 1A:
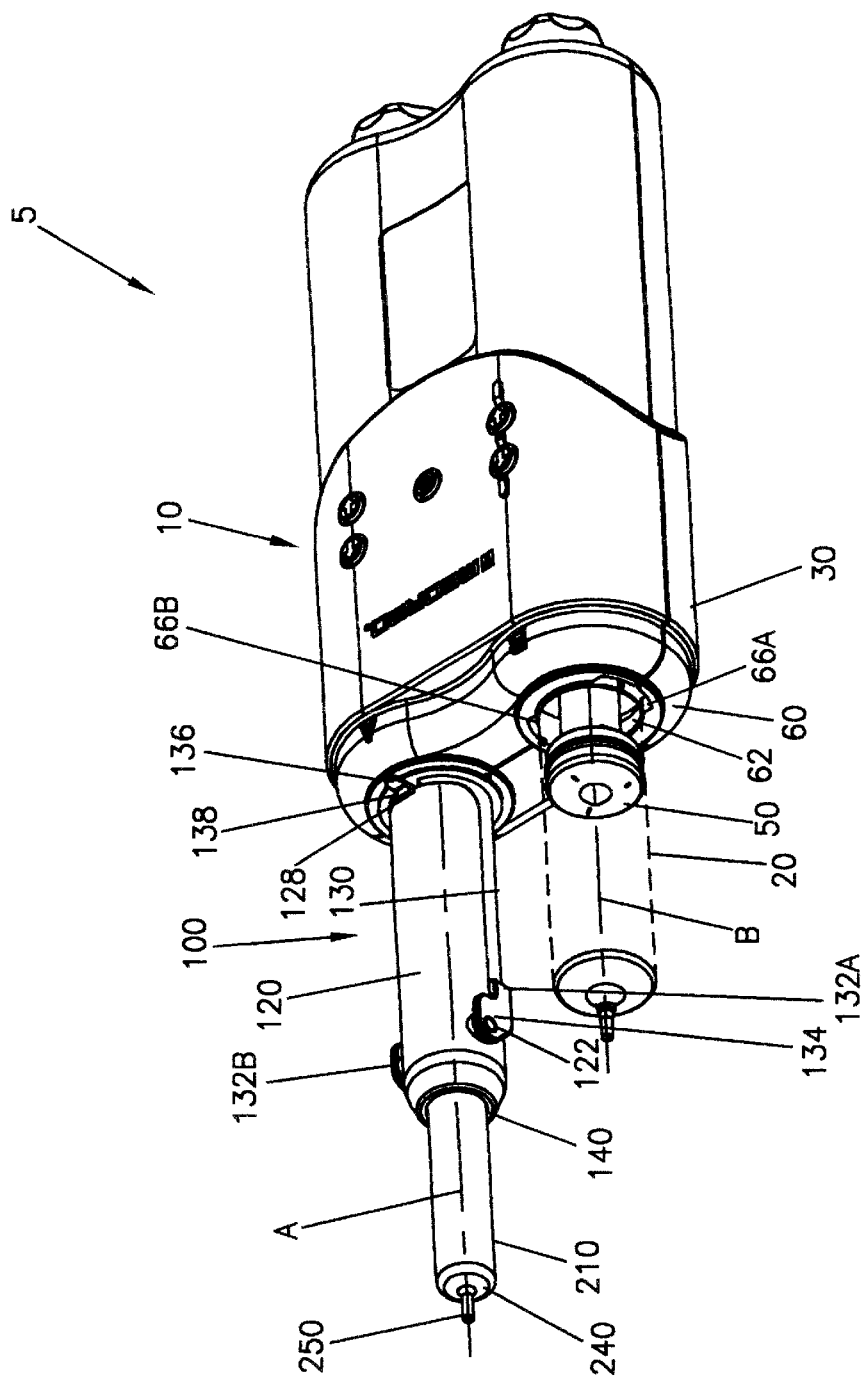
FIG. 1A illustrates an embodiment of an injector system of the present invention for use in connection with an MRI procedure.
Figure 1B:
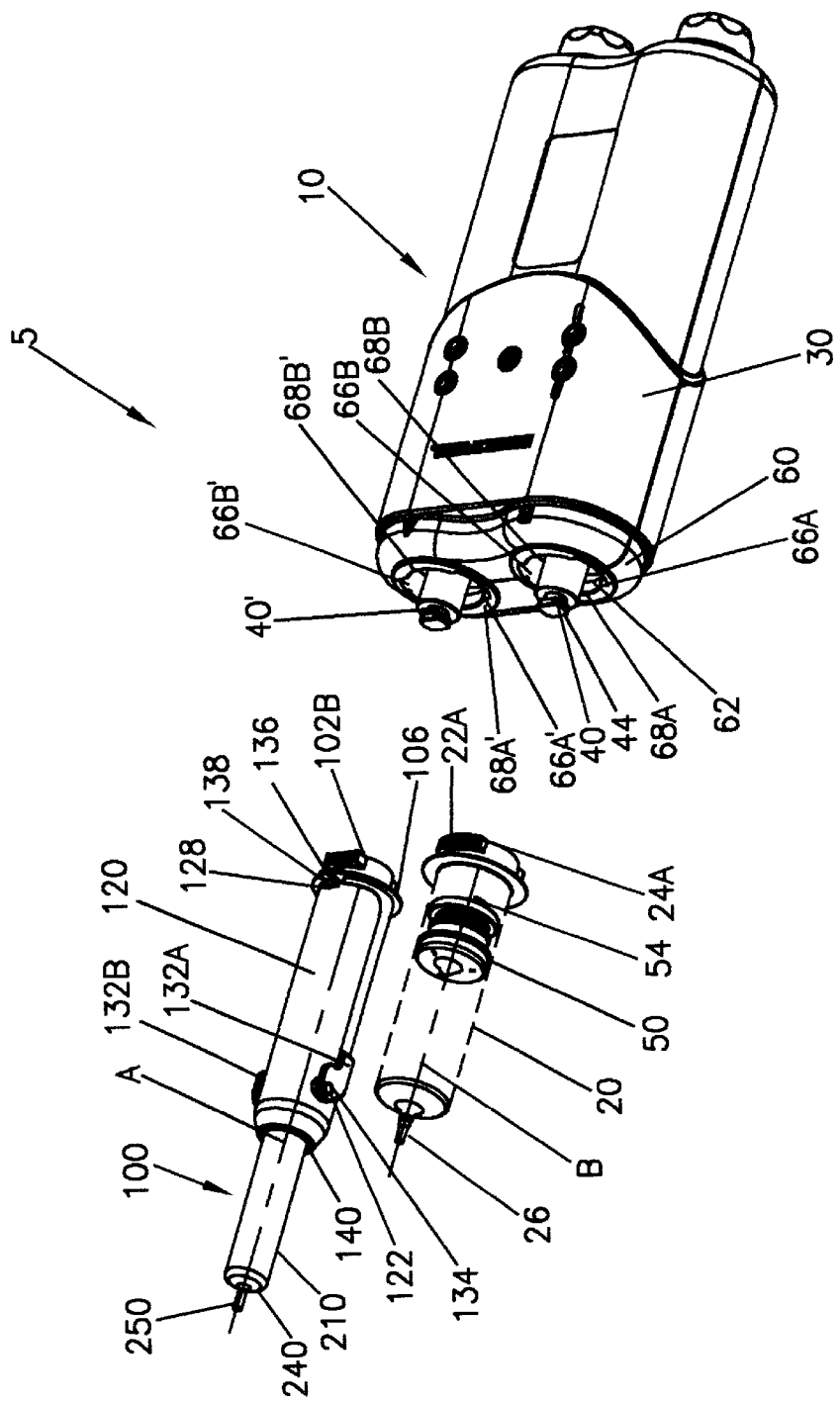
FIG. 1B illustrates the injector system of FIG. 1A in which the saline syringe and the adapter have been disassembled from the injector.

An embodiment of a front-loading injector system 5 of the present invention is illustrated in FIGS. 1A and 1B. Injector system 5 is particularly adapted for use in MRI procedures and includes a powered injector 10, a syringe 20 for injection of saline solution and an adapter 100. An example of an injector 10 suitable for use in the present invention is the SPECTRIS® injector available from Medrad, Inc. of Indianola, Pa. However, the present invention may be used in connection with other fluid delivery systems, including injectors and infusion pumps for computed tomography, ultrasound and angiographic procedures. As best illustrated in FIG. 1B, injector housing 30 of injector 10 preferably includes a first drive member or piston 40 therein which cooperates with a syringe plunger 50 in saline syringe 20 to inject a saline solution from the interior of syringe 20 into a patient.

As shown in FIG. 1B, injector 10 also includes a second drive member or piston 40' that cooperates with an adapter 100 and a syringe plunger extension rod 220 of a syringe 200 (see, for example, FIG. 2A) containing a fluid such as a contrast medium to inject the fluid from the interior of syringe 200 into a patient.

As used herein to describe injection system 5 and other embodiments of the present invention, the terms "axial" or "axially" refer generally to, for example, an axis A around which adapter 100 is preferably formed (although not necessarily symmetrically therearound) or an axis B around which saline syringe 20 is formed (although not necessarily symmetrically therearound). The terms "proximal" or "rearward" refer generally to an axial or a longitudinal direction toward the end of injector housing 30 opposite the end to which syringe 20 and adapter 100 are mounted. The terms "distal" or "forward" refer generally to an axial or a longitudinal direction toward a syringe tip of syringe 20 or syringe 200. The term "radial" refers generally to a direction normal to an axis such as axis A or axis B.

Saline syringe 20 and adapter 100 are preferably removably connected to injector 10 as described in U.S. Pat. No. 5,383,858. In that regard, front-loading injector 10 preferably includes a front wall 60 having a first opening 62 formed therein. Piston 40 is reciprocally mounted within injector 10 and is extendible through opening 62. Piston 40 preferably includes a piston flange or head 44. Receiving slots 66a and 66b, are preferably positioned opposite one another around opening 62. Receiving flanges 68a and 68b are preferably positioned opposite one another and between receiving slots 66a and 66b and extend inwardly into opening 62.

The rearward end of saline syringe 20 preferably includes a readily releasable mounting mechanism such as a pair of mounting flanges 22a and 22b for mounting saline syringe 20 in a desired position relative to the front wall 60 of injector 10. Flange 22b is not shown but is generally identical to flange 22a and positioned opposite flange 22a. Mounting flanges 22a and 22b may include indicating means, such as detent(s), bar code(s), protrusion(s) or notch(es) 24a, which provide information to the injector 10, for example, about the type of saline syringe 20 being used. Correspondingly, injector 10 preferably includes any suitable means (not shown) for reading information from notch(es) 24a.

To attach syringe 20 to injector 10, the rearward end of syringe 20 is inserted into injector opening 62 such that mounting flanges 22a and 22b are inserted into receiving slots 66a and 66b, respectively. If, at this time, plunger 40 is not positioned at the rearward end of syringe 20 such that a piston flange 44 can engage capture members 54 (as described in U.S. Pat. No. 5,383,858), piston 40 may be advanced forward by the operation of injector 10 until piston flange 44 is in position to be received by capture members 54.

Once mounting flanges 22a and 22b are inserted into receiving slots 66a and 66b, respectively, and piston 40 is in position to be received by capture members 54, the operator preferably rotates syringe 20 approximately 90 degrees such that mounting flanges 22a and 22b move behind and are engaged by receiving flanges 68a and 68b, respectively, and piston flange 44 rotates into position to be retained by, for example, L-shaped capture members 54. Injector 10 may include a stop mechanism (not shown), for example, extending from at least one of the retaining slots 68a and 68b, to prevent rotation of syringe 20 more than 90 degrees. Tactile, visual or audible feedback can be provided to the operator via, for example, cooperating members on syringe 20 and injector 10 to inform the operator that secure connection has been achieved. After securely attaching syringe 20 to injector 10, advancing piston 40 in a forward direction will apply a motive force to plunger 50 to advance plunger 50 forward within syringe 20, thereby forcing saline solution in syringe 20 out of syringe neck 26 into the fluid path to the patient. Retracting piston 40 in a rearward direction will cause plunger 50 to move rearward in syringe 20, thereby drawing fluid into syringe 20.

Adapter 100 is preferably attached to injector 10 in a similar manner as described above for attachment of syringe 20 to injector 10. In that regard, a rearward portion or section of adapter 100 preferably includes a readily releasable mounting mechanism such as a pair of mounting flanges 102a and 102b (see FIG. 2A) for mounting adapter 100 in a desired position relative to the front wall 60 of injector 10. Mounting flanges 102a and 102b may include indicating means, such as detents or notches 104a and 104b, which provide information to injector 10 about the type of adapter and/or syringe being used. Correspondingly, injector 10 preferably includes any suitable means (not shown) for reading information from notches 104a and 104b.

To attach adapter 100 to injector 10, the rearward end of adapter 100 is inserted into injector opening 62' such that mounting flanges 102a and 102b are inserted into receiving slots 66a' and 66b', respectively. Once mounting flanges 102a and 102b are inserted into receiving slots 66a' and 66b', respectively, the operator preferably rotates adapter 100 or adapter 100/syringe 200 combination approximately 90 degrees such that mounting flanges 102a and 102b move behind and are engaged by receiving flanges 68a' and 68b', respectively. As described above, a stop mechanism (not shown) may, for example, extend from at least one of the retaining slots 68a' and 68b', to prevent rotation of adapter 100 more than 90 degrees. Once again, tactile, visual or audible feedback can be provided to the operator via, for example, cooperating members on adapter 100 and injector 10 to inform the operator that secure connection has been achieved. A drip flange 106 can, for example, be formed on a rearward portion of adapter 100 to, among other things, assist in forming a secure connection. Drip flange 106 may, for example, include a raised member or detent 108 (see, for example, FIG. 2A) that mates with a recess (not shown) in the face of opening 62' to provide audible and/or tactile feedback to the operator upon proper alignment/connection of adapter 100 to injector 10.

After securely attaching adapter 100 to injector 10, advancing piston 40' in a forward direction will apply a motive force to a plunger extension 220 of syringe 200 to a advance syringe plunger 225 (see FIG. 2E) forward within syringe barrel 210, thereby forcing contrast medium in syringe 200 out of syringe neck 250 into the fluid path to the patient.

Adapter 100 is illustrated in further detail in FIGS. 2A through 2E. In the embodiment of adapter 100, a "break" action is used to load syringe 200 into a carrier 110 of adapter 100. In that regard, carrier 110 includes a first portion or section 120 and a second portion or section 130. First portion 120 is hingingly attached to second portion 130 via support arms 132a and 132b, each of which includes a passage 134 therein. First portion 120 includes generally cylindrical tabs 122 on each side thereof that snap into passages 134 to hingingly or rotatably attach first portion 120 to second portion 130 about an axis C (see, for example, FIG. 2D) preferably oriented generally perpendicular to longitudinal axis A of adapter 100.

Figure 2A:
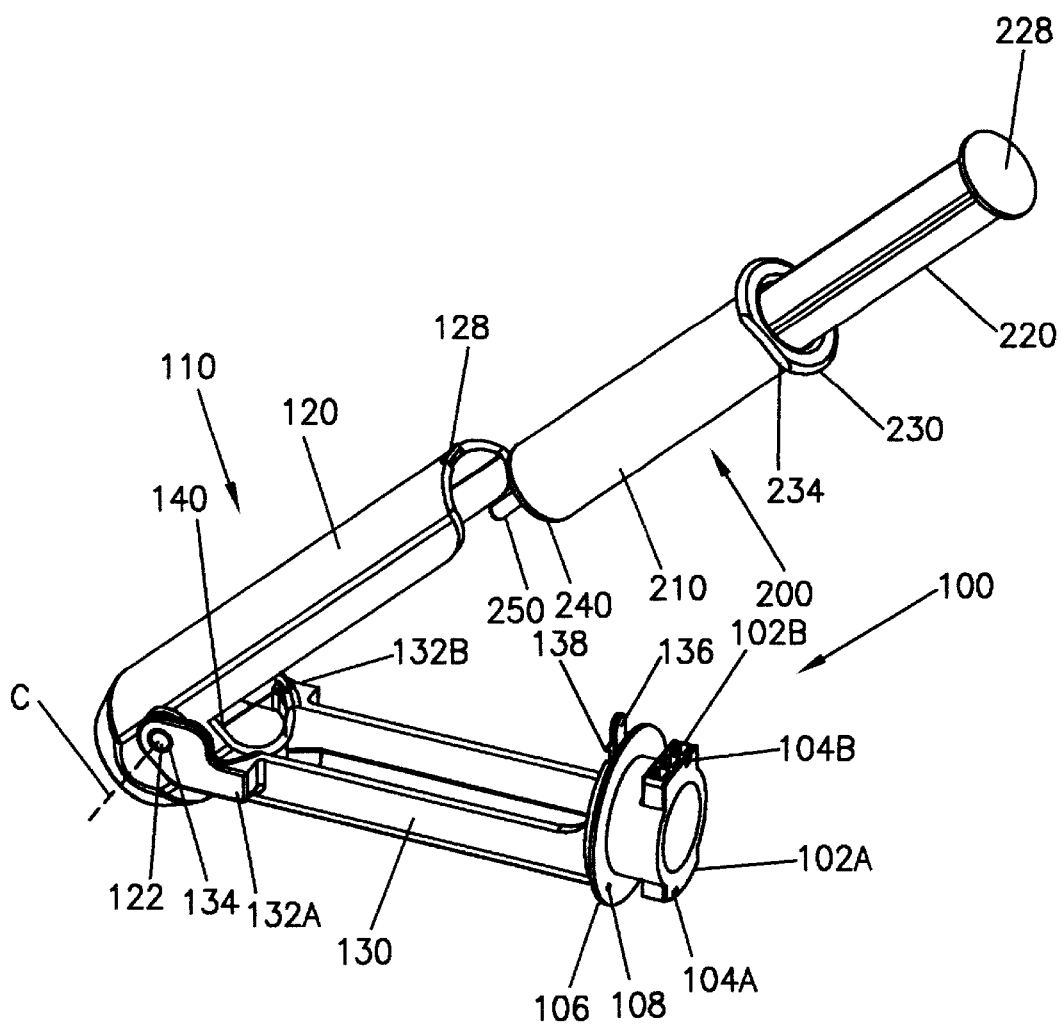
FIG. 2A illustrates a perspective view of an embodiment of an adapter of the present invention in an open state for loading of a syringe therein.

FIG. 2A illustrates adapter 100 in an open state and ready to receive syringe 200 from a position to the rear of the hinging mechanism. In this embodiment, syringe 200 comprises generally cylindrical body or barrel 210 in which a fluid such as contrast medium, saline or therapeutic agent is contained. Preferably, the fluid medium is "prefilled" into syringe 200 before loading of syringe 200 in adapter 100.

Syringe 200 can, for example, be prefilled by the manufacturer or manually filled remote from the injector. Syringe 200 further includes plunger 225 slideably disposed within barrel 210 that is similar in operation to plunger 50 of saline syringe 20. Plunger 225 of syringe 200 is operatively connected to plunger extension rod 220 by, for example, a threaded connection. Syringe 200 further includes a flange 230 at a rearward end of barrel 210. At a forward end of barrel 210, syringe 200 includes a generally frusto-conical transition or cone region 240 that connects barrel 210 to a tapered neck 250 from which contrast medium is injected. Tapered neck 250 can include, for example, a luer connection at the end thereof for connection to a fluid path (for example, flexible tubing) as known in the art.

In many cases, syringes 200 for use, for example, in an MRI procedure are prefilled with contrast medium by the manufacturer. Many such syringes 200 are designed for manual injection into a patient wherein an operator manually advances plunger rod 220 (and thereby plunger 225 within syringe 200) forward by applying pressure to a rearward end 228 of plunger extension rod 220. Syringe barrel 210 and flange 230 may, for example, be fabricated from glass or plastic. Plunger extension rod 220 is typically fabricated from a plastic material.

Figure 2B:
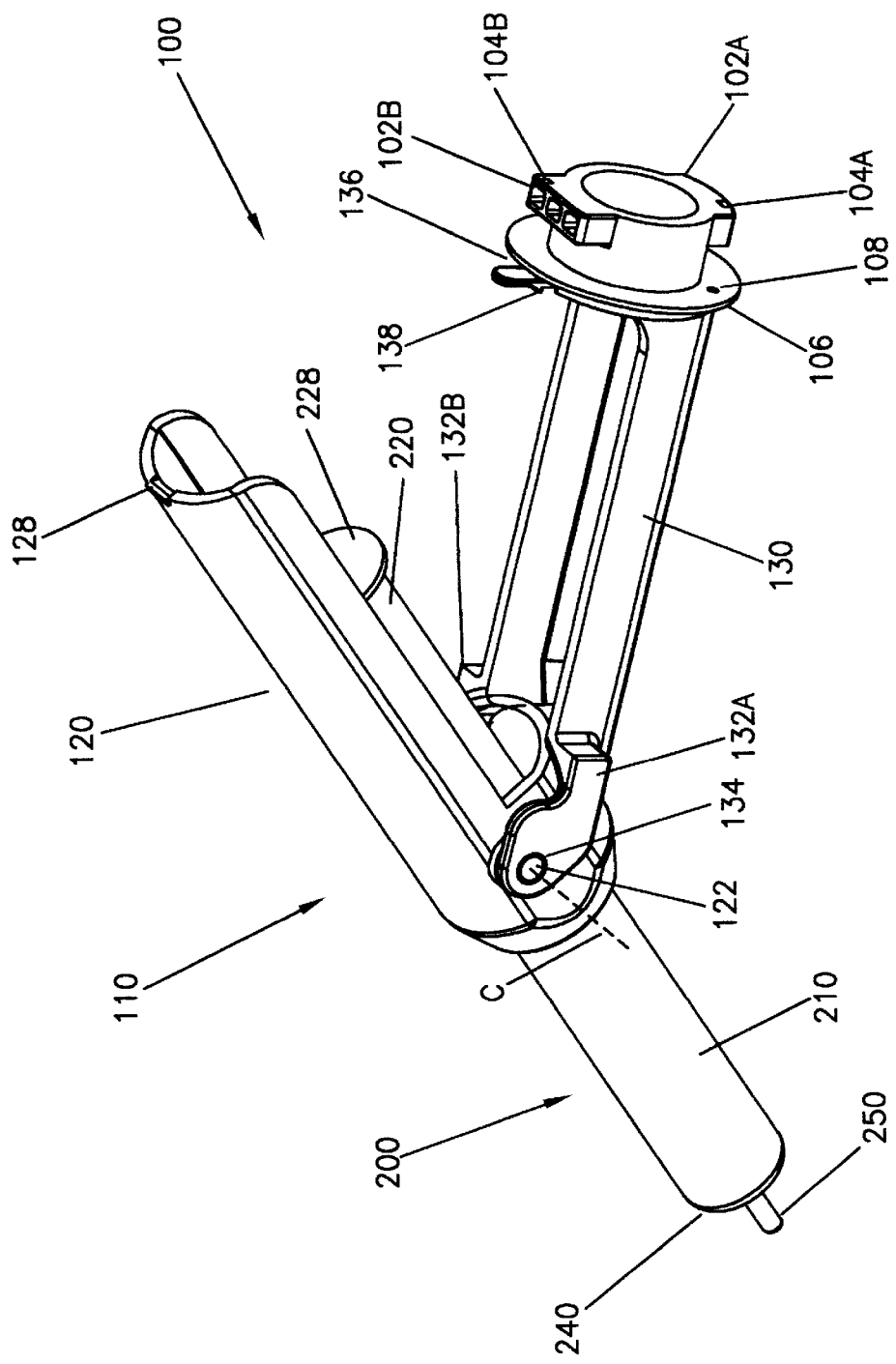
FIG. 2B illustrates a perspective view of the adapter of FIG. 2A in an open state with a syringe loaded therein.

As illustrated in FIGS. 2A and 2B, syringe 200 is loaded into carrier 110 by positioning syringe 200 in general alignment with a generally cylindrical passage 140 formed in a forward end of first portion 120 of adapter 100. Syringe 200 is slid forward within passage 140 until syringe flange 230 abuts a shoulder 150 (see FIG. 2E) that extends radially inwardly within first portion 120. Shoulder 150 cooperates with syringe flange 230 to hold syringe 200 within adapter 100 and to provide resistance to the forward force applied to plunger extension rod 220 by piston 40' during an injection procedure.

Figure 2C:
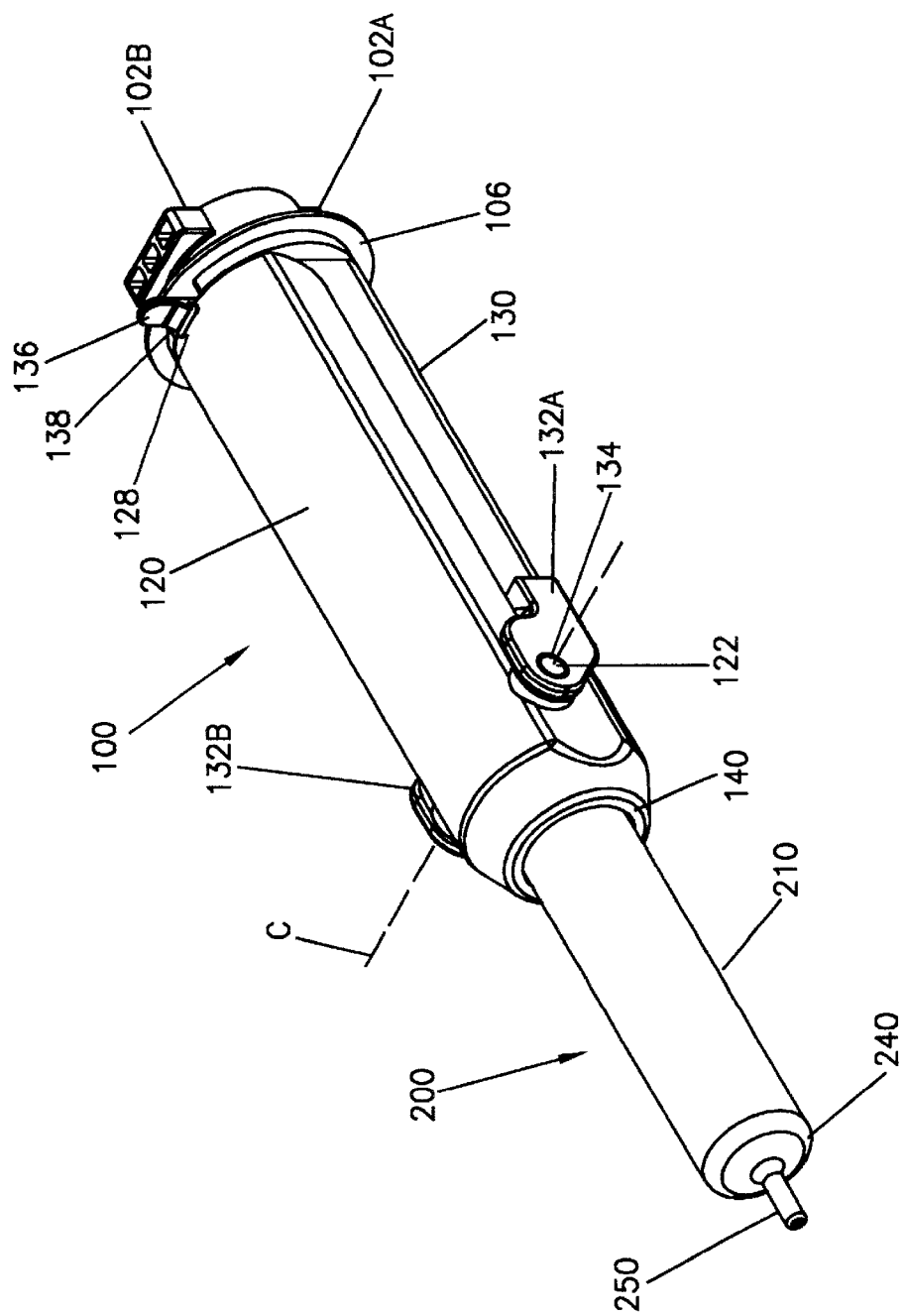
FIG. 2C illustrates a perspective view of the adapter of FIG. 2A in a closed state with a syringe loaded therein.
Figure 2D:
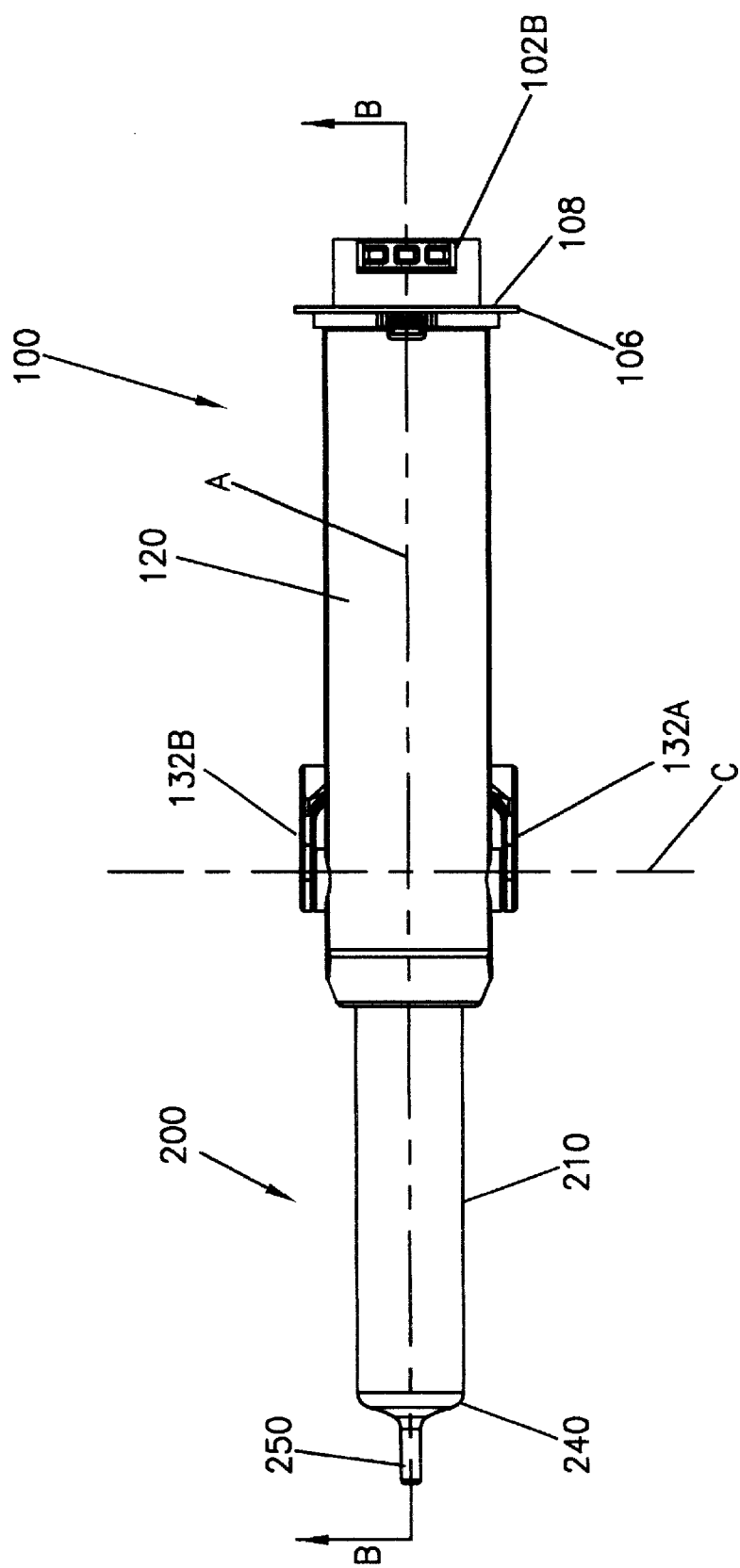
FIG. 2D illustrates a plan view of the adapter of FIG. 2A in a closed state with a syringe loaded therein.
Figure 2E:
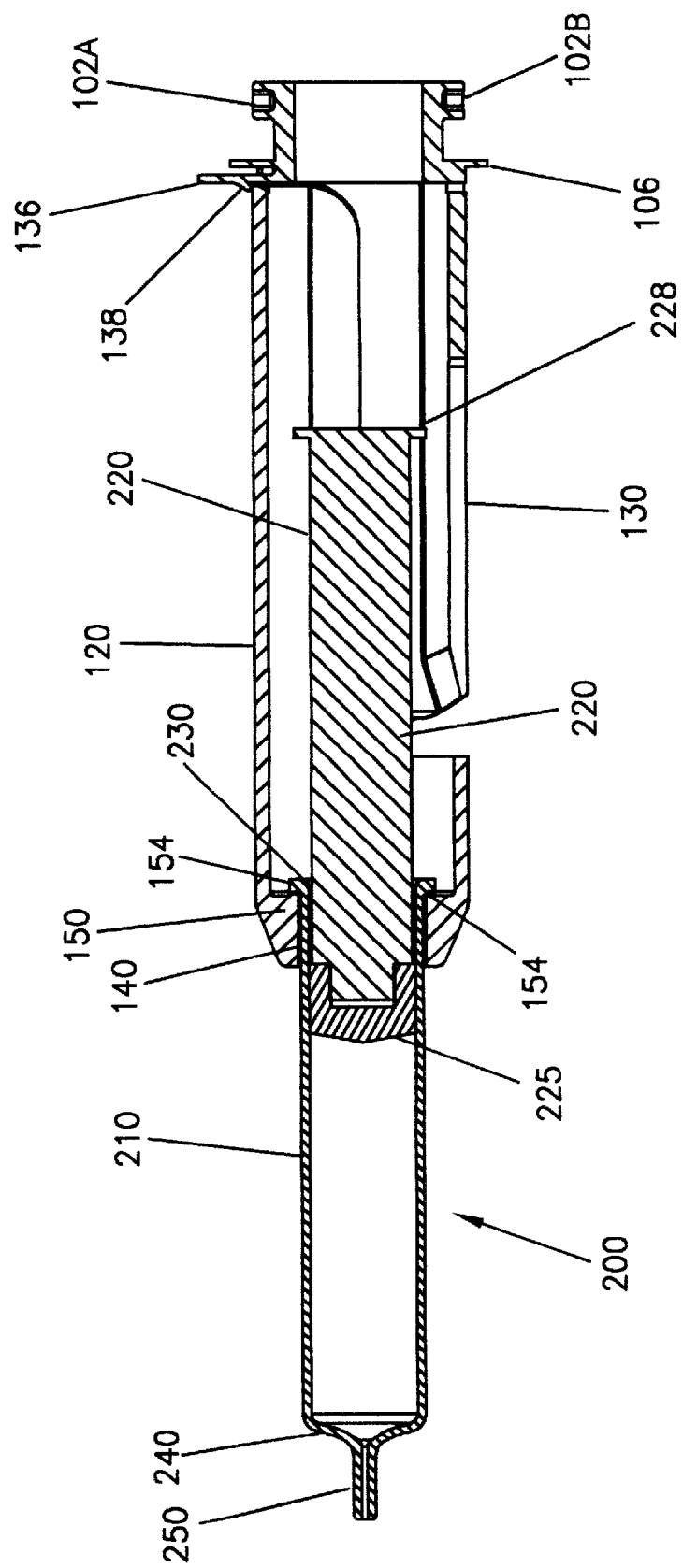
FIG. 2E illustrates a side, cross-sectional view of the adapter of FIG. 2A in a closed state with a syringe loaded therein.

As best illustrated in FIG. 2E, shoulder 150 preferably includes a rearward extending ridge portion 154 on the inner radius thereof so that ridge portion 154 contacts flange 230 only near or in the vicinity of the transition of syringe flange 230 into syringe barrel 210. Contact of ridge portion 154 with syringe flange 230 near barrel 210 assists in minimizing the forces placed upon cantilevered flange 230. For example, in the case of glass syringes 200, flange 230 may fail (break) if contact with shoulder 150 is made at or near the outer end of syringe flange 230, whereas the shorter lever arm resulting from contact with syringe flange 230 at or near the inner radius thereof will reduce the force on syringe flange 230 and prevent failure. Ridge portion 154 can be made of a resilient or compliant material such as an elastomeric material that can be different from the material of the remainder of adapter 100 to further reduce the likelihood of failure.

In the case of a prefilled syringe 200, there is no need for the operator to retract the plunger of syringe 200 to load syringe 200 with contrast medium. Therefore, there is usually no need for a follower mechanism in the adapter of the present invention to attach to plunger extension rod 220 to enable retraction of plunger 225 as described in connection with the adapter of U.S. Pat. No. 5,520,653. Piston 40' can simply be advanced to abut rearward surface 228 of plunger extension rod 220. Any further forward motion of piston 40' will result in advancement of the plunger of syringe 200 and pressurization of the contrast medium with syringe 200. Elimination of a carrier mechanism for the plunger extension simplifies and reduces the cost of manufacture of the adapters of the present invention as compared, for example, to the adapter of U.S. Pat. No. 5,520,653. Nevertheless, the adapters of the present invention may readily be configured with follower mechanisms that connect to plunger extension rods 220 to allow plunger retraction.

FIGS. 2C through 2E illustrate syringe 200 within adapter 100 with first portion 120 and second portion 130 in a closed position. Adapter 100 preferably includes a mechanism to assist in maintaining first portion 120 and second portion 130 in a closed position during operation of injector 100. Second portion 130 may, for example, include a latch tab 136 having an abutment shoulder 138 that cooperates with a recess 128 in a rearward end of first portion 120 to create a snap latching mechanism. Many other closing mechanisms can be used to maintain first portion 120 and second portion 130 in a closed position, as clear to one skilled in the art.

Closed carrier 110 created by first portion 120 and second portion 130 also functions to limit the motion of plunger extension rod 220 out of alignment with axis A. This prevents plunger extension rod 220 from, for example, slipping out of contact with piston 40', prevents deforming of plunger extension rod 220 and prevents eccentric loading of plunger extension rod 220. Deflection, eccentric loading or deforming of plunger extension rod 220 may, for example, cause leaking of fluid to the rear of plunger 225 or breaking of syringe 200. Radially inward projecting guide(s) can be formed in one or both of first portion 120 and second portion 130 to maintain even tighter tolerances. A section of either or both of first portion 120 and second portion 130 can be "cut away" to form a window for viewing of syringe extension rod 220. Likewise, a portion or the entirety of either or both first portion 120 and second portion 130 can be transparent.

Preferably, one or both of first portion 120 and second portion 130 includes an abutment member to prevent rotation of syringe 200 within carrier 110. It is, for example, desirable to prevent rotation of syringe 200 after connection thereof to fluid path tubing. Prevention of syringe rotation can also maintain syringe 200 in proper orientation for viewing, for example, volume gradations on syringe 200. One or more sides of first portion 120 can, for example, have a flattened profile to conform to flattened section(s) 234 of syringe flange 230 to prevent rotation of syringe 200.

As illustrated in FIGS. 2B through 2E, a substantial portion of syringe 200 extends forward through passage 140 so that syringe barrel 210 is plainly visible to the operator. Such visibility, for example, facilitates reading of wording printed on the syringe as well as visual determination of the volume of contrast remaining in syringe 200. Visibility of syringe 220 also allows the operator to more readily determine whether air is present in syringe 200 before commencing an injection procedure. Moreover, operators typically like to see plunger 225 in motion to provide reassurance that the injection is proceeding. Extension of a portion of syringe 200 beyond carrier 110 also facilitates grasping of syringe 200 by the operator to, for example, connect or disconnect a fluid path to syringe neck 250.

As illustrated, for example, in FIGS. 2A through 2C, axis C of rotation of the hinge mechanism (that is, the axis passing through the radial center of generally cylindrical tabs 122 in the embodiment of FIG. 2A) is preferably positioned such that the force experienced by carrier 110 during forward advancement of piston 40' tends to force or maintain carrier 100 in a closed position. The axis of cylindrical tabs 122 is preferably, for example, positioned above the center line or longitudinal axis of carrier 110 such that a forward force exerted on shoulder 150 tends to produce a torque that maintains first portion 120 in a latched, closed position relative to second portion 130.

Once an injection procedure is completed, the operator can grasp the adapter or adapter/syringe combination and rotate it 90 degrees back to the pre-installation orientation, thereby, disengaging mounting flanges 102a and 102b from behind receiving flanges 68a and 68b, respectively. The adapter/syringe combination is then removable from the injector 10.

Retaining syringe 200 within carrier 110 by abutment with shoulder 150, allows accommodation of many different designs of syringe 200 by carrier 110. Adapter 100 is thus usable with a wide variety of currently available syringes 200.

FIGS. 3A through 3E illustrate another embodiment of an adapter 300 for use with a syringe 200. The rearward portion of adapter 300 is essentially identical to that of adapter 100 and is removably attached to injector 10 as described above. Unlike adapter 100, which holds syringe 200 within adapter 100 and provides resistance to the forward force applied to plunger extension rod 220 by abutment of syringe flange 230, syringe 200 is held within adapter 300 and resistance provided to the forward force applied to plunger extension rod 220 by abutting a forward facing surface of forward transition region 240 of syringe 200 rather than by abutting or retaining syringe flange 230.

Like adapter 200, a hinging or "break" action is used to load syringe 200 into a carrier 310 of adapter 300. In that regard, carrier 310 includes a first portion 320 and a second portion 330. First portion 320 is hingingly or rotatably attached to second portion 330 via support arms 332a and 332b, each of which includes a passage 334 therein. First portion 320 includes generally cylindrical tabs 322 on each side thereof that reside in passages 334 to hingingly attach first portion 320 to second portion 330. First portion 320 rotates about an axis C that runs generally through the radial centers of tabs 322 and is generally perpendicular to the longitudinal axis A of adapter 300.

Figure 3A:
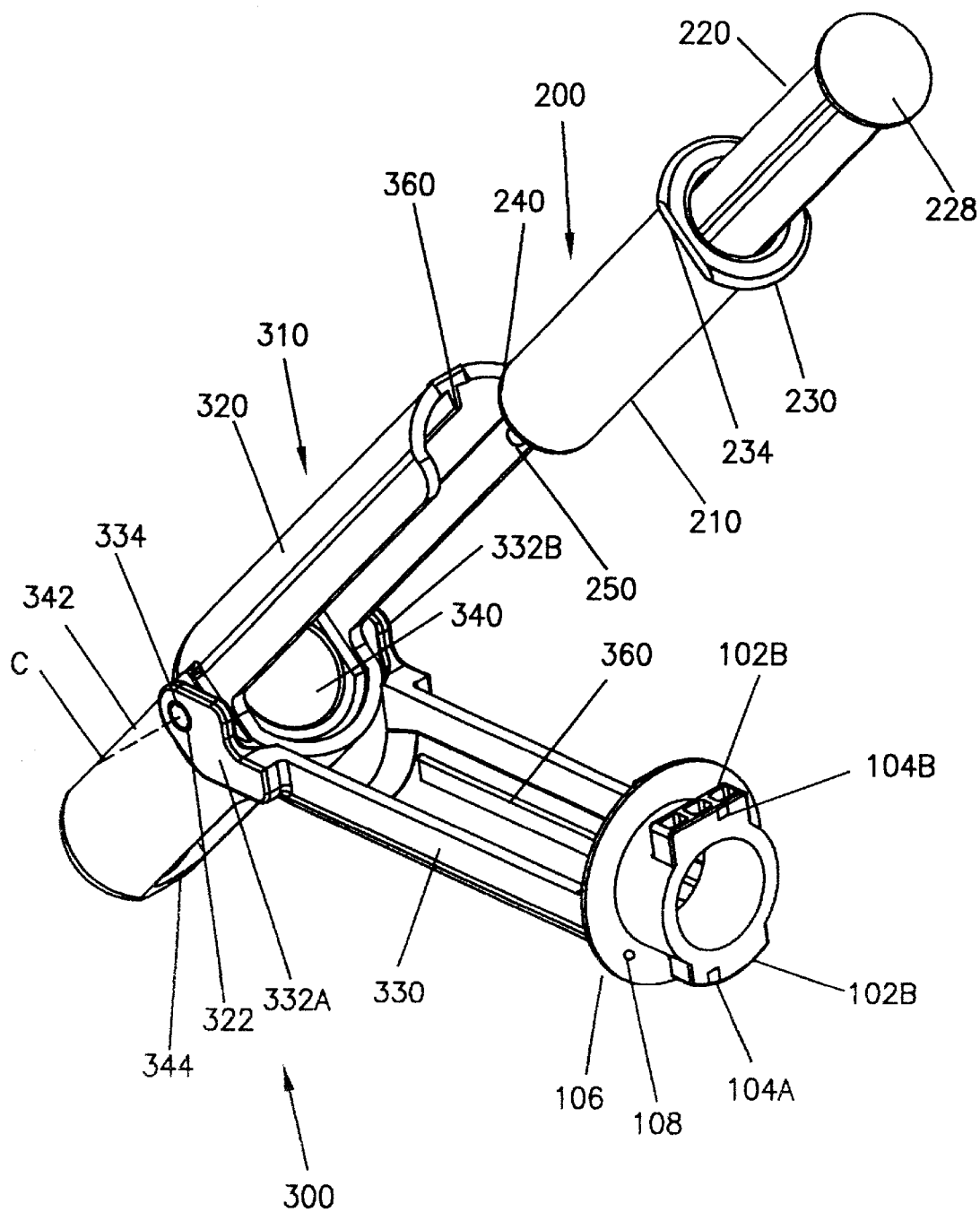
FIG. 3A illustrates a perspective view of another embodiment of an adapter of the present invention in an open state for loading of a syringe therein.
Figure 3B:
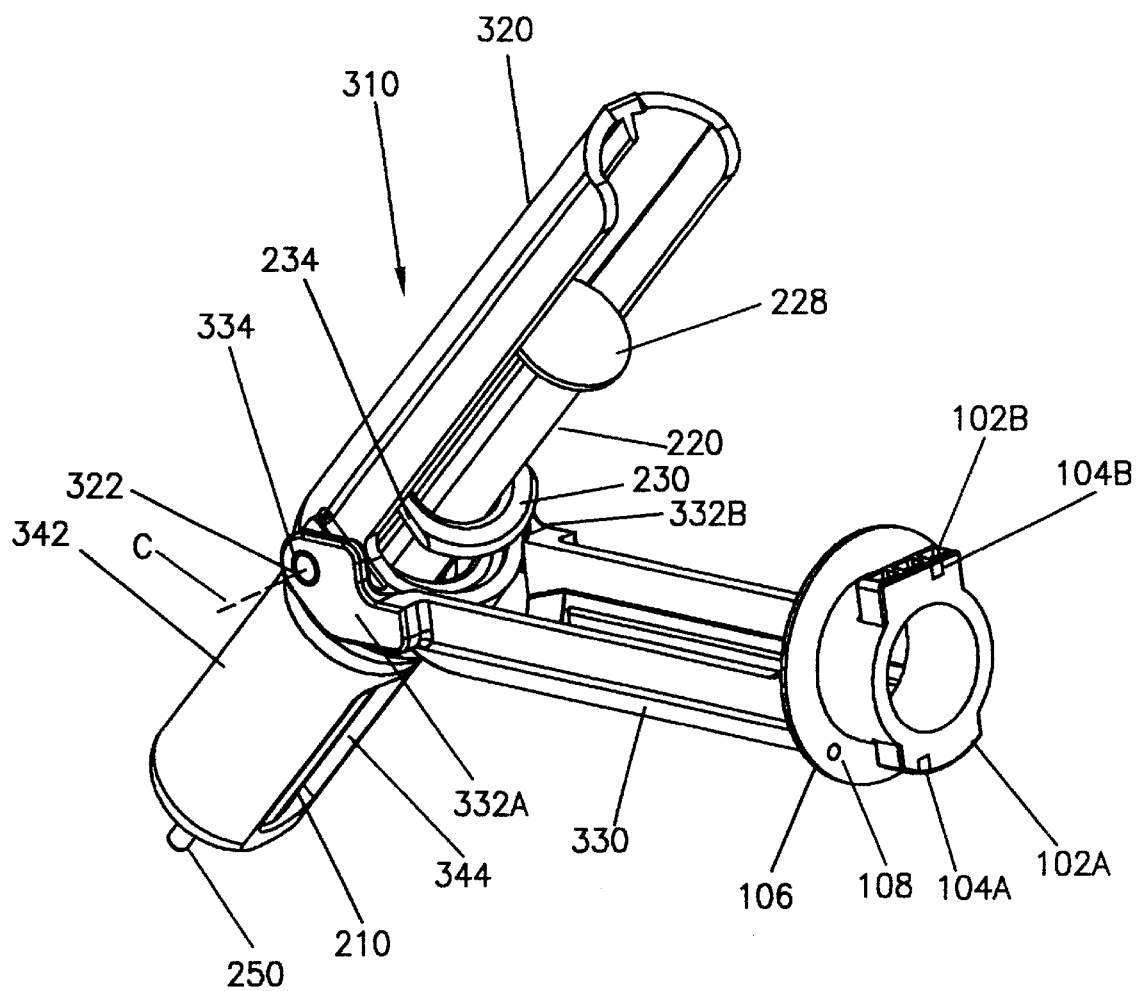
FIG. 3B illustrates a perspective view of the adapter of FIG. 3A in an open state with a syringe loaded therein.
Figure 3C:
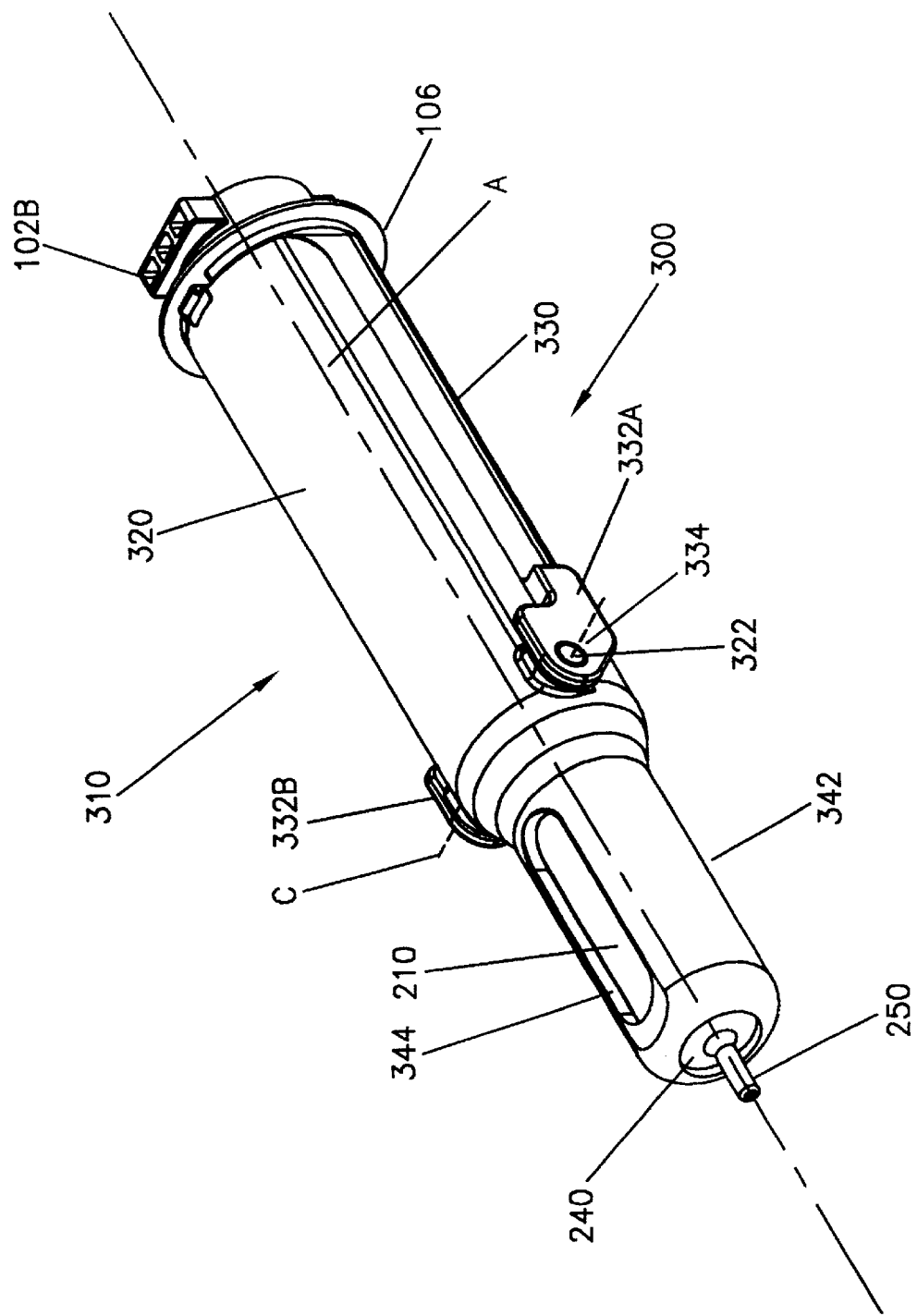
FIG. 3C illustrates a perspective view of the adapter of FIG. 3A in a closed state with a syringe loaded therein.
Figure 3D:
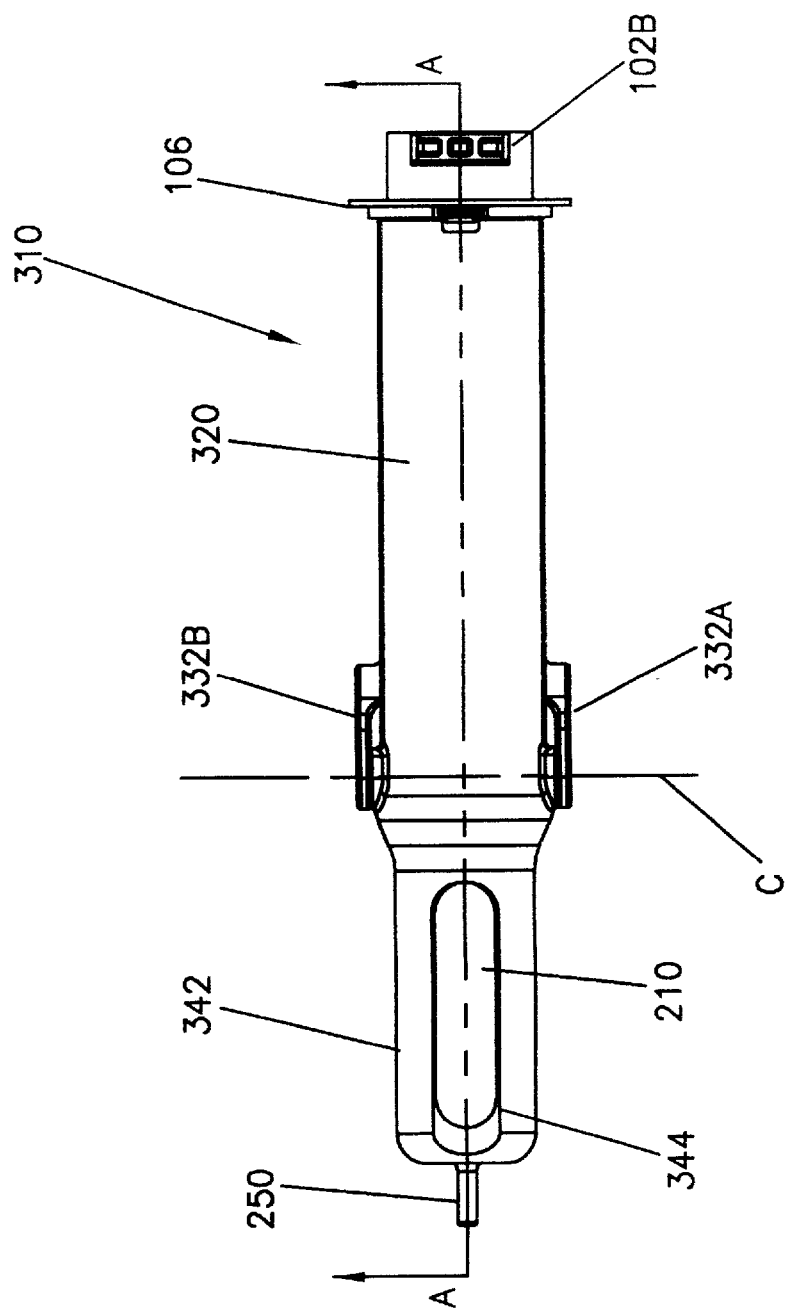
FIG. 3D illustrates a plan view of the adapter of FIG. 3A in a closed state with a syringe loaded therein.
Figure 3E:
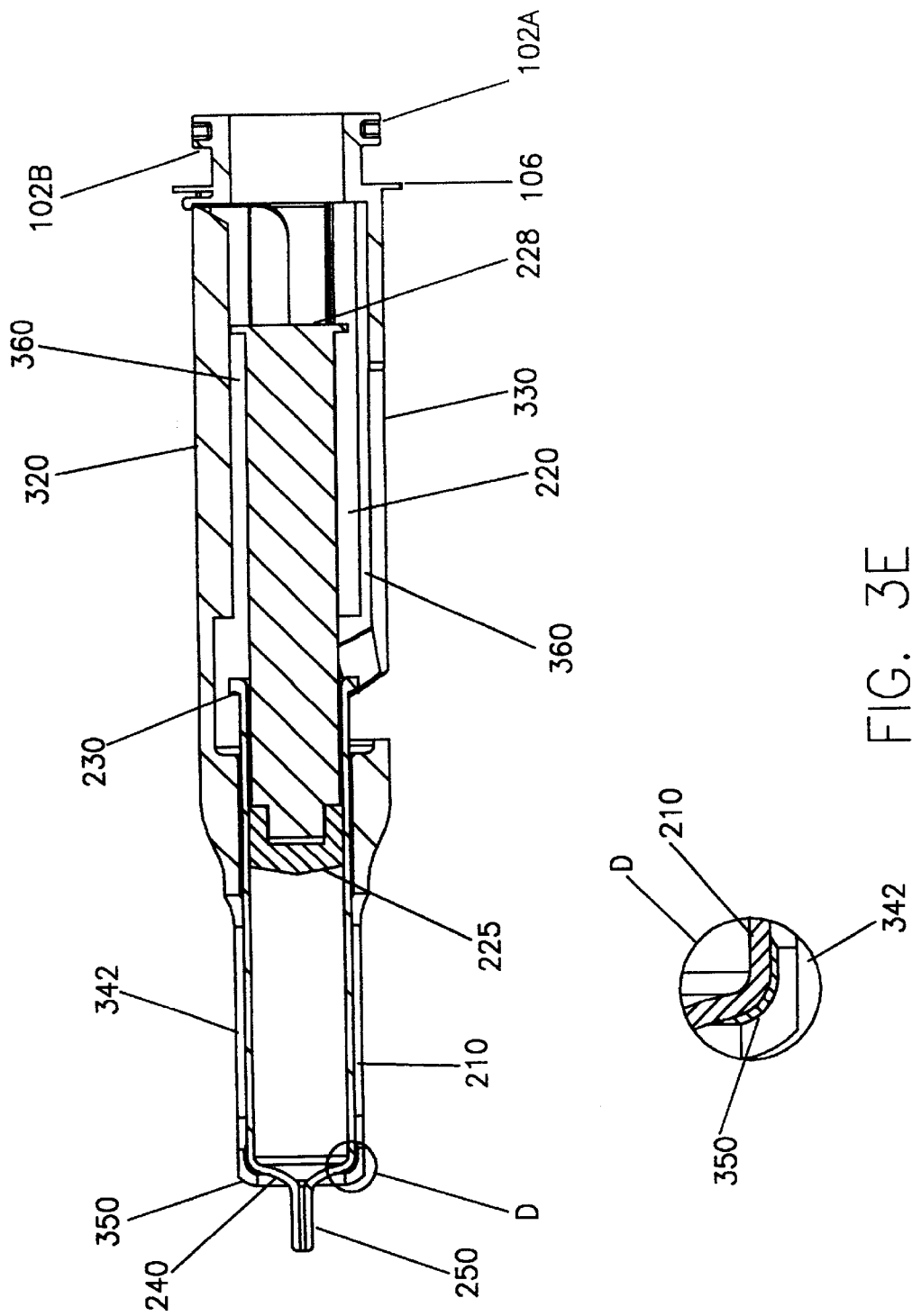
FIG. 3E illustrates a side, cross-sectional view of the adapter of FIG. 3A in a closed state with a syringe loaded therein.

FIG. 3A illustrates adapter 300 in an open state and ready to receive syringe 200. As illustrated in FIGS. 3A and 3B, syringe 200 is loaded into carrier 310 by positioning syringe 200 in general alignment with a generally cylindrical passage 340 formed in first portion 320 of adapter 300. Syringe 200 is slid forward within passage 340 until a forward facing surface of syringe 200 abuts a retention shoulder 350 (see FIG. 3E) that extends radially inward at a forward end of a forward portion 342 of first portion 310. Shoulder 350 cooperates with forward syringe transition region or cone 240 to hold syringe 200 within adapter 300 and to provide resistance to the forward force applied to plunger extension rod 220 by piston 40' during an injection procedure. As illustrated in detail D of FIG. 3E, shoulder 350 preferably contacts syringe 200 only near to or in the vicinity of the transition from the sidewall of barrel 110 to transition region 240 to take advantage of increased structural strength in this region. The contact area of shoulder 350 can be made of a resilient or compliant material (for example, an elastomeric material) to absorb energy and reduce the likelihood of breaking syringe 200.

Syringe 200 may be inserted in adapter 300 before connection of adapter 300 to injector 10. Alternatively, syringe 200 may be loaded into adapter 300 while adapter 300 is mounted on injector 10. Indeed, adapter 300 may remain mounted on injector 10 through many different injection procedures with different syringes.

Forward portion 342 preferably includes one or more open areas or windows 344 so that syringe barrel 210 is plainly visible to the operator. All or a portion of forward portion 342 can also be transparent to further facilitate viewing of syringe barrel 210. Open areas 344 also facilitate grasping of syringe 200 by the operator to, for example, connect or disconnect a fluid path to syringe neck 250. As described in connection with adapter 100, one or both of first portion 320 and second portion 330 may include an abutment member to prevent rotation of syringe 200 within carrier 310. For example, the side(s) of first portion 320 can have a flattened profile to conform to flattened section(s) 234 of syringe flange 230 to prevent rotation of syringe 200. The cooperation of such a flattened profile of carrier 310 and section 234 can, for example, be used to ensure a desired orientation of syringe barrel 210 with open areas 344. For example, two open areas 344 can be provided generally opposing each other (that is, positioned approximately 180° apart on forward portion 342). The cooperation of a flattened profile of carrier 310 and flattened syringe flange section 234 in this embodiment preferably allows mounting of syringe 200 in carrier 310 in only two axially rotated orientations, 180° apart.

One or a plurality of inward projecting guide 360 can be formed in one or both of first portion 120 and second portion 130 to maintain a tight tolerances to prevent deflection of plunger extension rod 330 as discussed above. A plurality (for example, three) guides 360 can be used about first portion 120 and/or second portion 130 to limit or prevent deflection in any direction.

Open areas (not shown) can also be provided on carrier 310 in the area where syringe flange 230 resides to accommodate large (in a radial direction) or irregularly shaped syringe flanges 230. Such open areas preferably extend longitudinally to accommodate syringes of different length from a forward end thereof to the syringe flange thereof. In general, the adapters of the present invention preferably provide adequate capacity to accommodate syringes of widely varying length, diameter, etc.

An important function of an injector is to monitor and report the actual volume of fluid available for delivery within a syringe. This function, for example, enables rapid decision on whether enough fluid is present to proceed with an imaging procedure or whether additional volume should be loaded. Monitoring the cumulative volume of fluid delivered to a patient is also desirable for certain applications where a recommended per-patient dosage volume should not be exceeded. Fluid volumes delivered by injectors are typically displayed in 1.0 ml increments and are tracked by the injector with finer resolution than is displayed. Injectors also preferably detect and differentiate among different types and sizes of syringes so that accurate display and delivery of fluid volume is provided.

To achieve such fluid volume management specifications, an adapter or syringe must be installed on an injector, be oriented in a known manner and provide the control system with identification information. Identification can be provided by coded features on the adapter or syringe that are detected by sensors on the injector so that each adapter and/or syringe is known by its code and fluid volume parameters specific to that syringe are implemented. When syringes 200 that are intended for non-powered, hand injection are installed on power injector 10, adequate identification is still preferably provided. This result can be achieved by first placing syringe 200 in adapter 100 or 300 which facilitates mounting on injector 10 and possesses its own unique code as encoded by, for example, the positions of notches 104a and 104b. In this manner, many different types and sizes of syringes 200 and/or adapters can be accommodated.

Syringes 200 are frequently of similar geometry such that more than one type of syringe 200 can be carried by the same adapter, giving rise to the potential of incorrect identification and possible fluid delivery error by injector 10. However, it is desirable to minimize the number of adapters required to accommodate all the hand syringes intended for a specific injector leading to a need to install more than one volume of syringe per adapter, provided individual functionality can be achieved. Syringes that share the same functional internal diameter, but have different lengths of travel can be treated as equivalent if both are referenced to the adapter, and consequently to injector 10, by a front-most surface thereof (that is, cone or transition region 240). If syringes 200 sharing the same functional diameter but having different lengths are referenced to the adapter injector 10 by rear flange 230 only, injector 10 will not be able to determine where the front of a syringe 200 is and cannot accurately determine/report the volume of contrast medium available. Mounting hand syringes 200 by rear flange 230 as in the embodiment of adapter 100 thus preferably requires one adapter per syringe diameter and length combination, which results in a larger number of adapters than would be required using a front mounting as in the embodiment of adapter 300. Multiple adapter combinations decrease the ease of use for an operator and expand the logic and sensing capacity required of injector 10. An optimum approach would be to use a single adapter that accommodates all hand syringes targeted for a particular injector. To approach this goal, it is preferable to retain/abut a front end of syringes 200 as described above in connection with adapter 300 so that injector 10 can determine the position of the front end of syringe 200. Loading of a front end of syringe 200 is also preferred to take advantage of an area of increased syringe strength to prevent syringe failure.

Figure 4A:
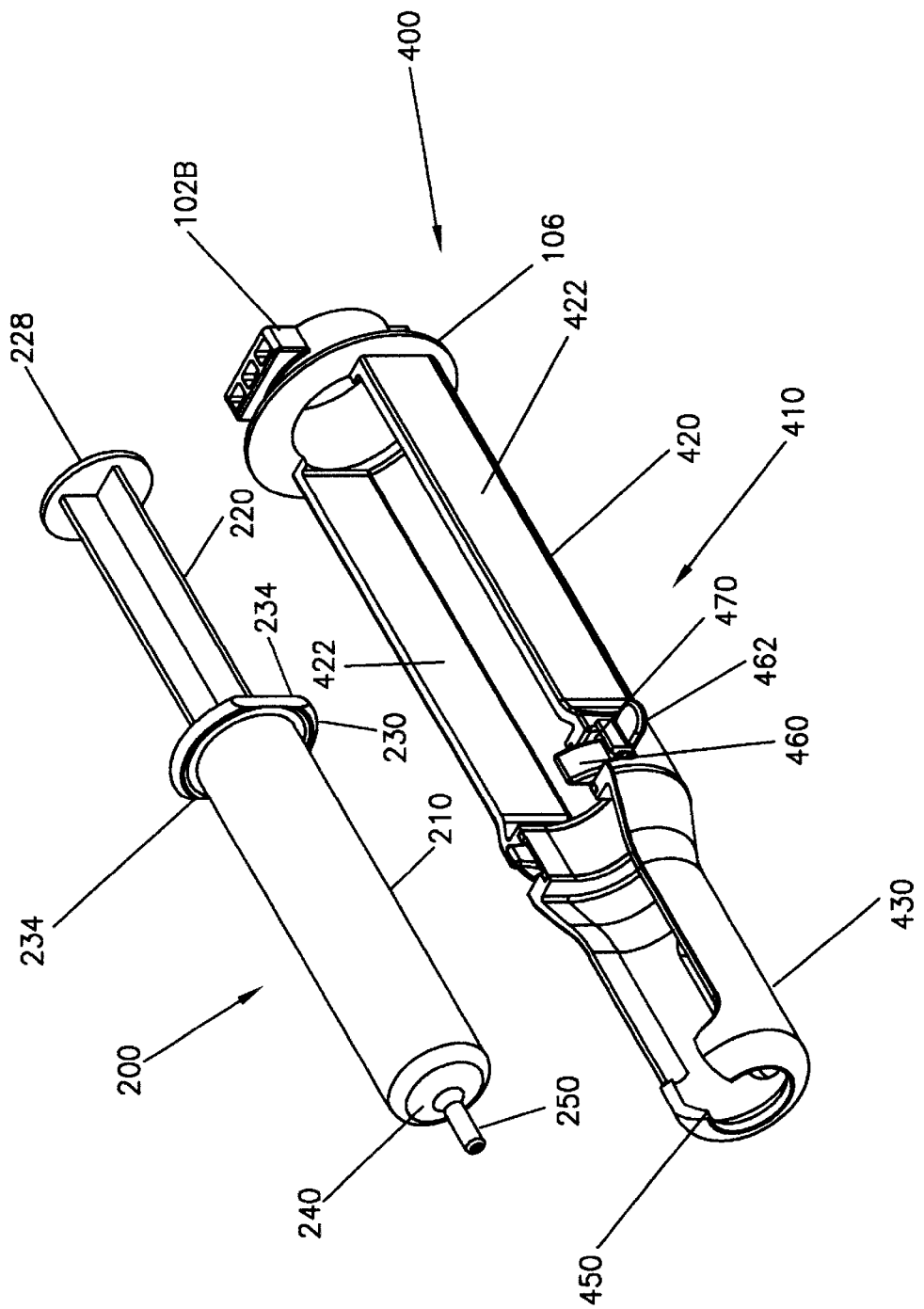
FIG. 4A illustrates a perspective view of another embodiment of an adapter of the present invention with a syringe positioned to be inserted therein.
Figure 4B:
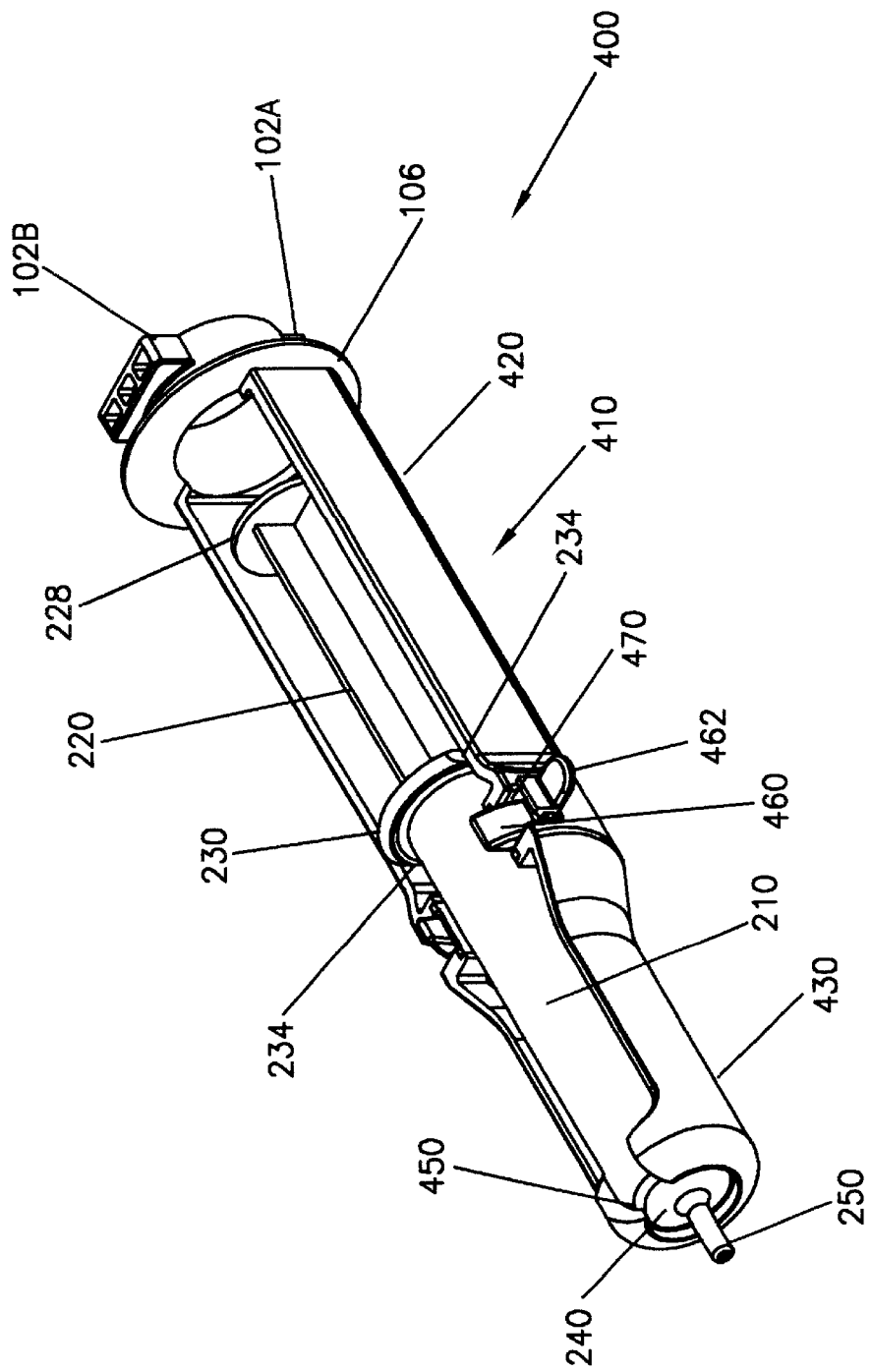
FIG. 4B illustrates a perspective view of the adapter of FIG. 4A with the syringe positioned therein.
Figure 4C:
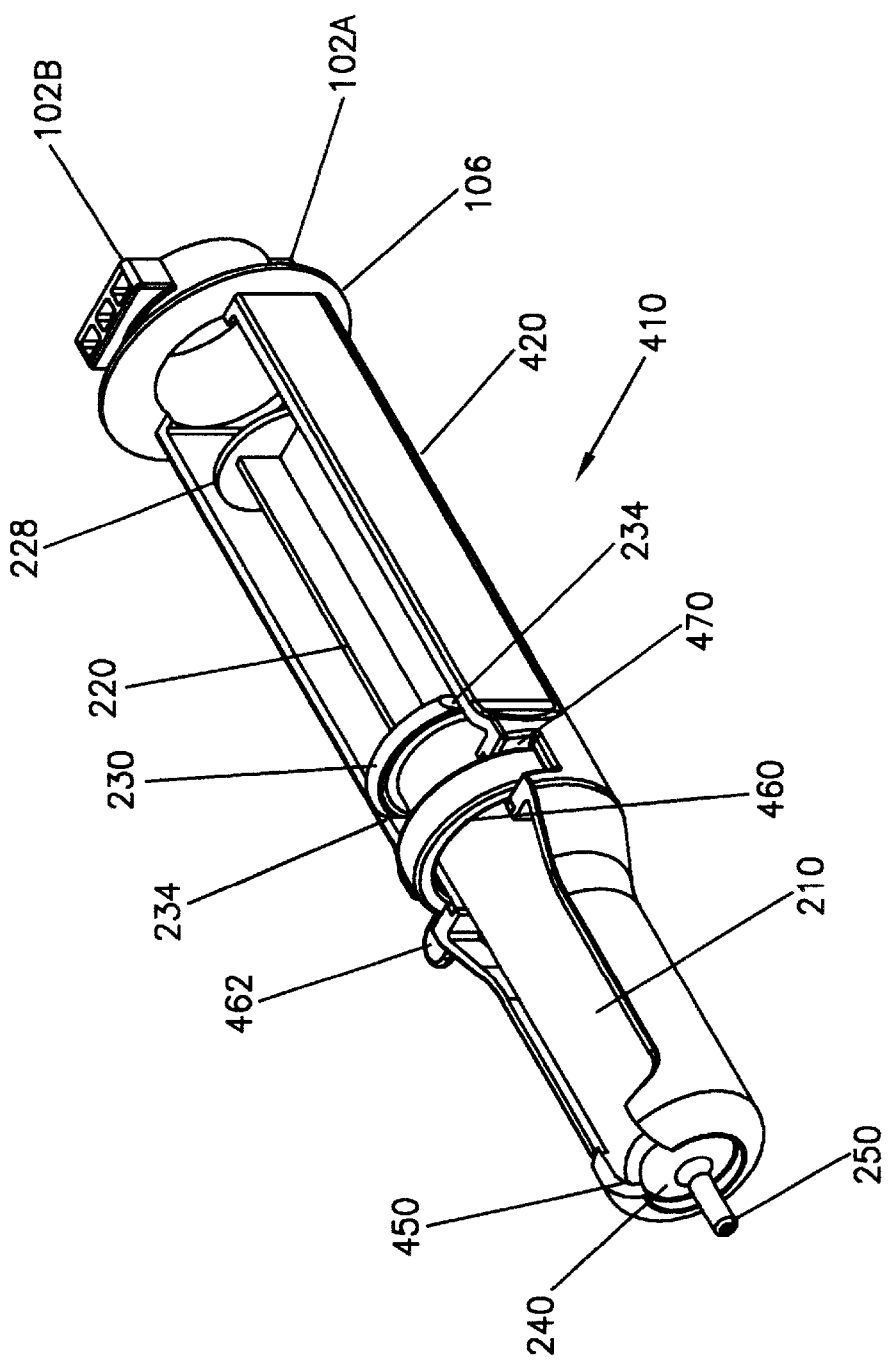
FIG. 4C illustrates a perspective view of the adapter of FIG. 4A wherein a syringe retaining member is in a closed position.

FIGS. 4A through 4C illustrate another embodiment of an adapter 400 for use with syringe 200. The rearward portion of adapter 400 is essentially identical to that of adapters 100 and 300 and is removably attached to injector 10 as described above. Unlike adapters 100 and 300, which incorporate a hinging action to enclose syringe 200, syringe 400 includes an open carrier 410. Like adapter 300, however, syringe 200 is held within adapter 400 and resistance provided to the forward force applied to plunger extension rod 220 by abutting forward transition or cone region 240 of syringe 200.

As illustrated in FIGS. 4A and 4B, syringe 200 is simply loaded into adapter 400 by dropping syringe 200 therein from above. Adapter 400 preferably includes a first, rearward portion 420 that seats/supports syringe flange 230. Preferably, first portion 420 has generally flat side walls 422 that cooperate with generally flat sections 234 on syringe flange 230 to restrict or substantially prevent rotation of syringe 200 within adapter 400. Side walls 422 of first portion 420 preferably extend upward past the generally common axis of syringe 200 and adapter 400 to assist in supporting syringe 200.

Adapter 400 further includes a second, forward portion 430 that seats/supports syringe barrel 210. Second portion 430 preferably includes a radially inward extending abutment shoulder 450 that abuts cone or transition region 340 of syringe 200 to retain syringe 200 within adapter 400 and provide resistance to the forward force applied to plunger extension rod 220 by piston 40'. Although second portion 430, including abutment shoulder 450, are open on the top thereof, the generally cylindrical wall of second portion 430 and abutment shoulder 450 preferably extend upward past the generally common axis of syringe 200 and adapter 400 to support resistance of the forward force applied to plunger extension rod 220 and to prevent deflection of syringe 200 out of alignment with the shared axis of syringe 200 and adapter 400.

Through abutment shoulder 450, adapter 400 provides the benefits of forward abutment of syringe 200 discussed above. Moreover, because adapter 400 is open along its entire axial length, insertion and removal of syringe 200 is facilitated. For example, syringe 200 can even be easily removed from adapter 400 while still connected to a fluid path (not shown in FIGS. 4A through 4C). In some cases, however, it may be desirable to form abutment shoulder 450 to contact a forward facing surface of transition region 240 around its entire circumference to provide additional stability. In that case, the forwardmost end of carrier 410 would be closed and any fluid path would preferably be disconnected before removing syringe 200 from adapter carrier 410.

Figure 4D:
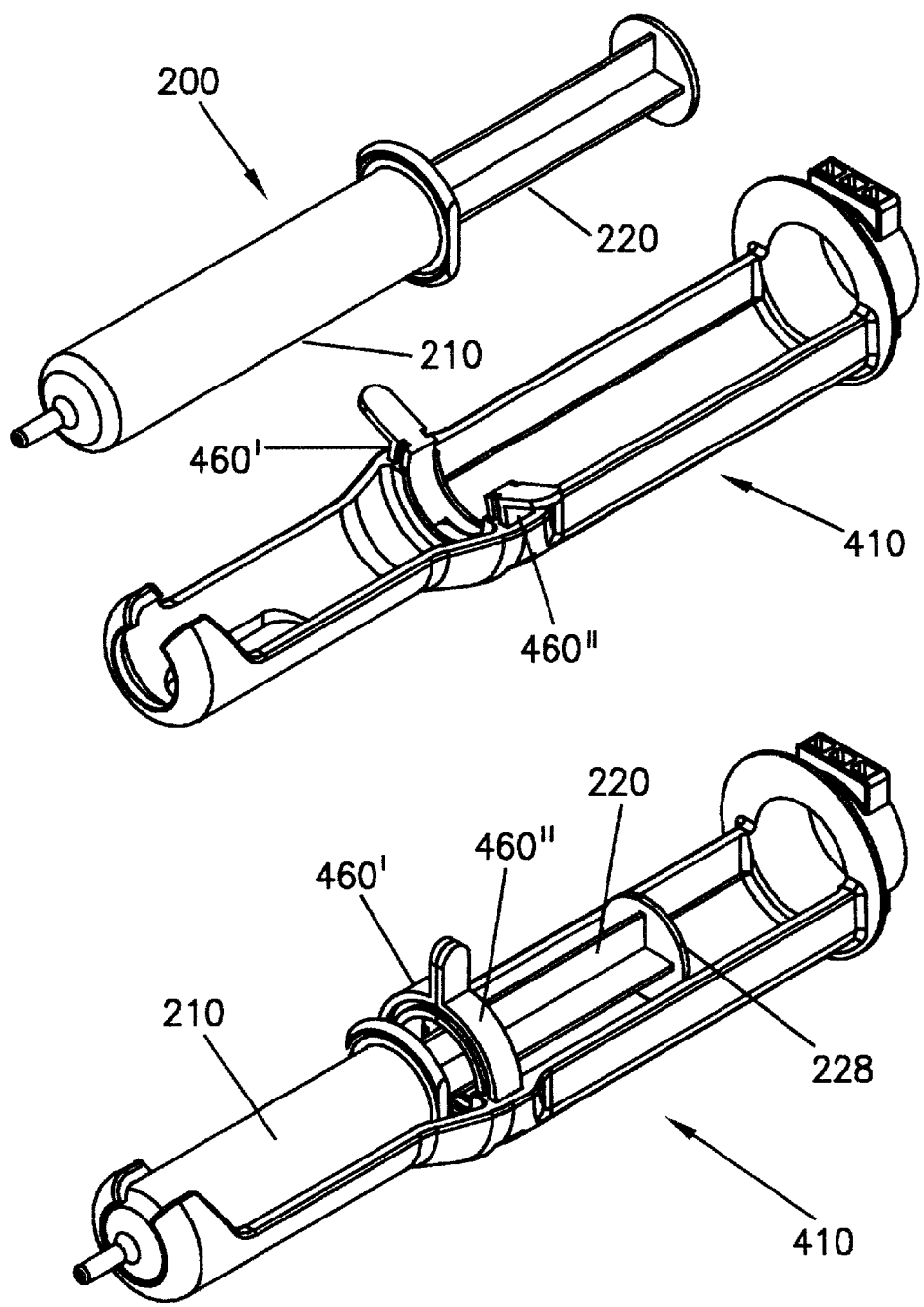
FIG. 4D illustrates a perspective view of an adapter including another embodiment of a syringe retaining member.

Adapter 400 preferably further includes at least one retaining member 460 to assist in retaining and/or stabilizing syringe 200 in proper alignment therein. Retaining member 460 is slideably retained in a generally cylindrically shaped passage 470 in carrier 410. Retaining member 460 is illustrated in an open or disengaged position in FIGS. 4A and 4B. To close or engage retaining member 450 to retain syringe 200, the operator can supply force to collar tab 462 to rotate retaining member 450 within passage 470 to a closed position as illustrated in FIG. 4C. In another embodiment illustrated in FIG. 4D, rotatable retaining member 460 can be split into two portions 460' and 460'' that rotate to meet in the middle.

Figure 4E:
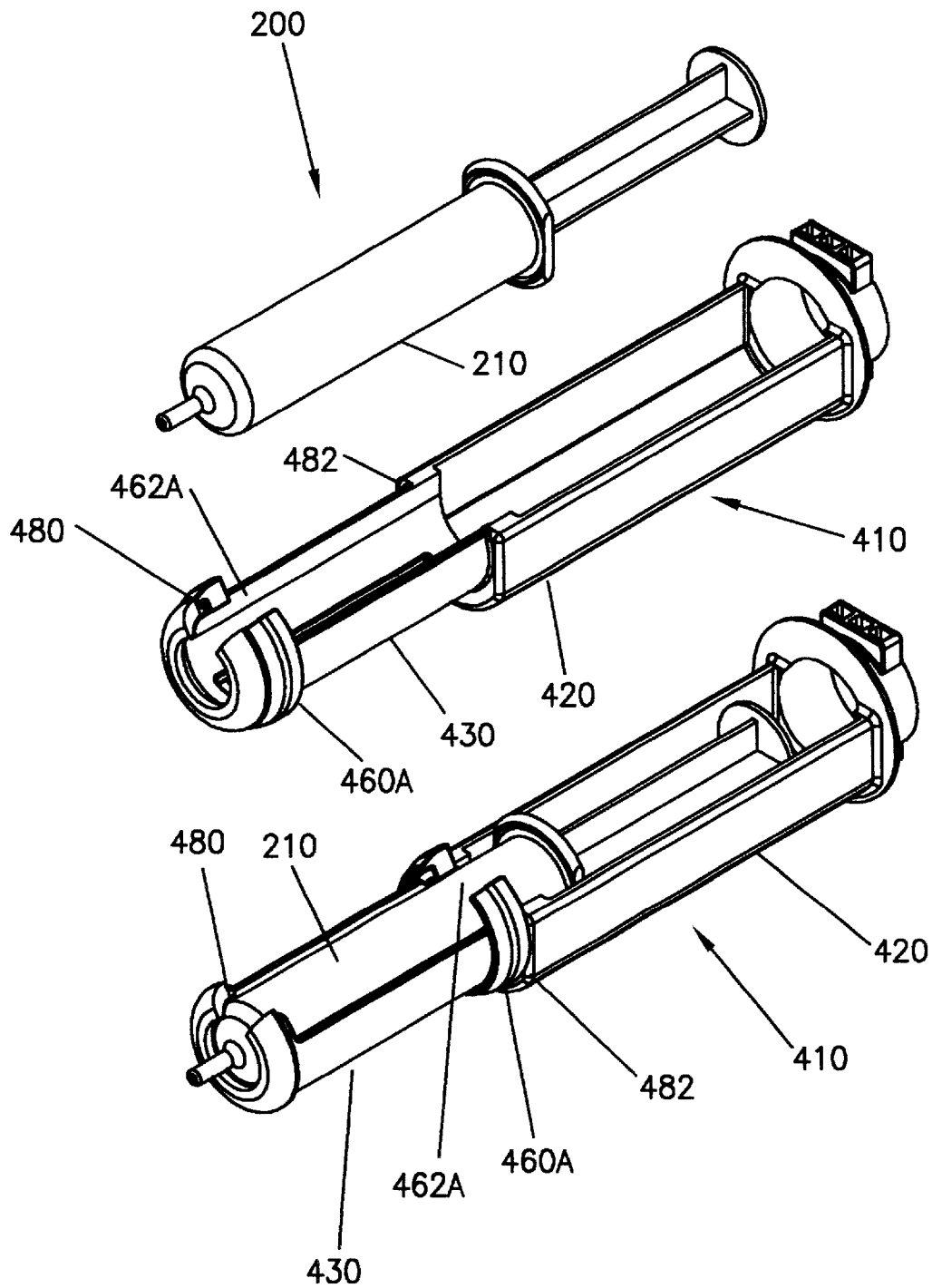
FIG. 4E illustrates a perspective view of an adapter including another embodiment of a syringe retaining member.

Other retaining/stabilizing members or mechanisms for retaining/stabilizing syringe 200 are illustrated in FIGS. 4E through 4I. In FIG. 4E a sliding retaining member 460a is positioned on/around second, forward portion 430 of carrier 410. Retaining member 460a is preferably positioned at a forwardmost position on second portion 430 when syringe is loaded into carrier 410 to facilitate loading. Retaining member 460a is retained on second portion 430 by abutment with a forward shoulder 480 and rearward shoulder 482. After seating of syringe 200, retaining member 450a can preferably be slid to any desired position on second portion. Positioning retaining member 460A at a rearwardmost position on second portion 430 may maximize stability. Retaining member 460a preferably conforms closely to the shape of syringe barrel 210 to maximize stability. Retaining member 460a may include an open section 462a on the top thereof to facilitate removal of syringe 200 from carrier 410 without disconnection of an attached fluid path element.

Figure 4F:
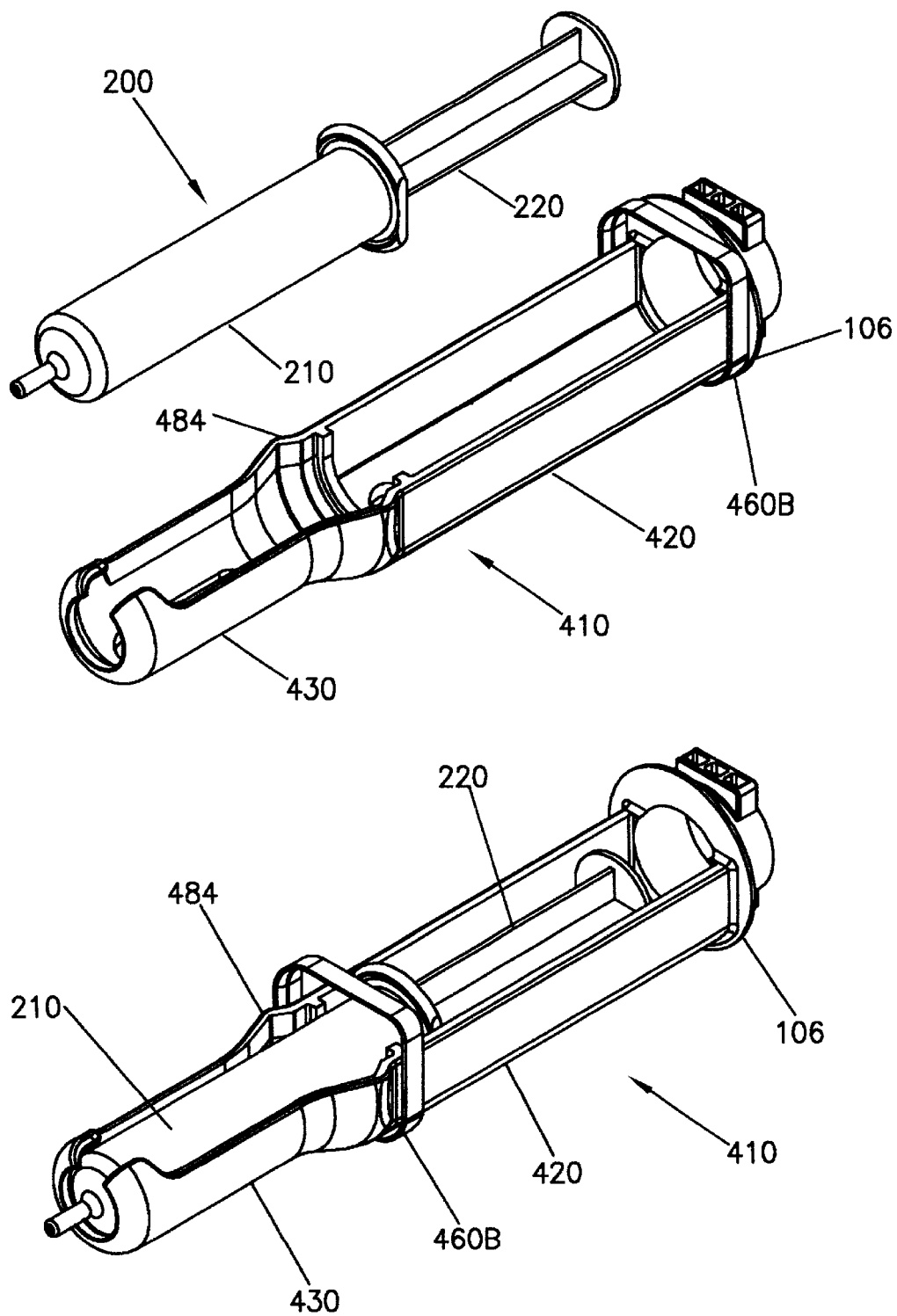
FIG. 4F illustrates a perspective view of an adapter including another embodiment of a syringe retaining member.

FIG. 4F illustrates another embodiment of a slideable retaining member 460b. Retaining member 460b is slideably retained upon first portion 420 of carrier 410 between drip flange 106 and shoulder 484. To facilitate loading of syringe 200, retaining member 450b may be positioned near drip flange 106. After loading of syringe 200, retaining member 460b can be slid to a desired position. An opening (not shown) in retaining member 460b can be formed to facilitate removal of syringe 200 from carrier 410 without disconnection of an attached fluid path element.

Figure 4G:
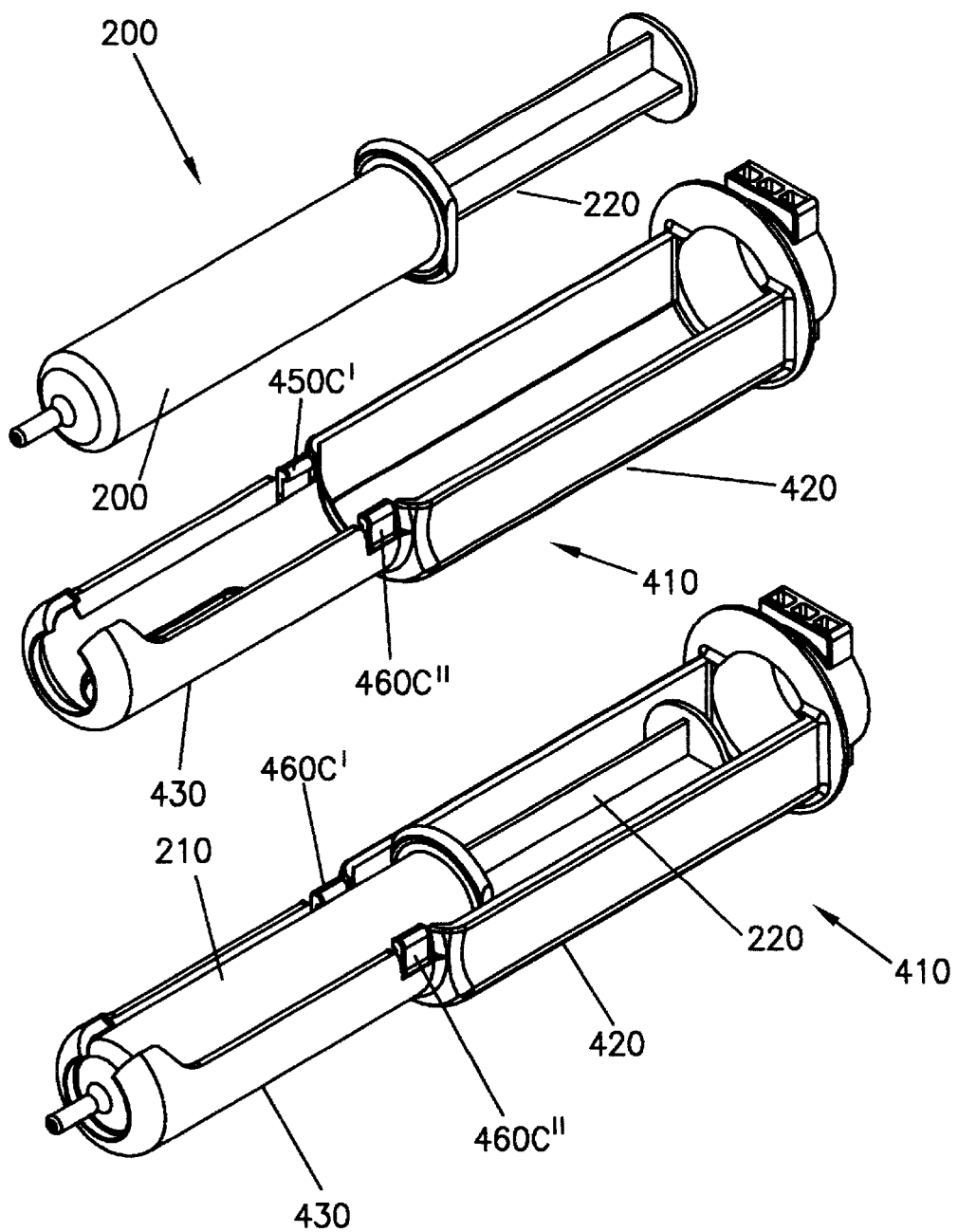
FIG. 4G illustrates a perspective view of an adapter including another embodiment of a syringe retaining member.

In the embodiment of FIG. 4G, a retaining mechanism includes two cantilevered retaining member 460c' and 460c'' that snap around syringe barrel 210 upon loading of syringe 200 in carrier 410.

A plurality of retaining/stabilizing members as described above can be provided along the length of carrier 410 to assist in retaining/stabilizing syringe barrel 210 and plunger extension rod 420 in proper position within carrier 410. The opening and closing of such retaining members can be operated individually or collectively, for example, via a common tab.

Figure 4H:
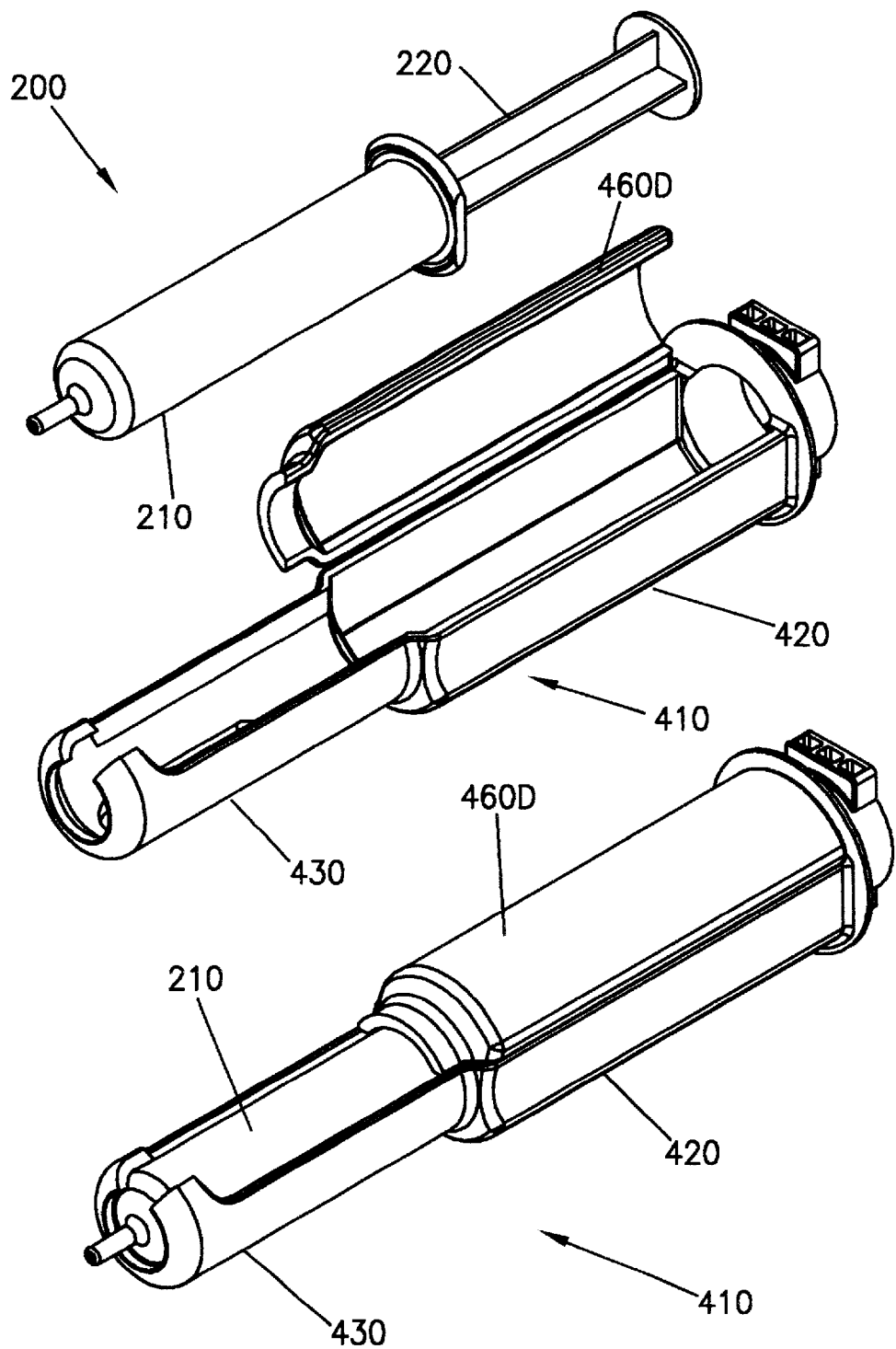
FIG. 4H illustrates a perspective view of an adapter including another embodiment of a syringe retaining member.

Alternatively, a retaining/stabilizing member can be increased in axially length to increase stability. For example, FIG. 4H illustrates a retaining member 460d hingingly attached to first portion 420 that extends along the entire length of first portion 420 and partially along the length of second portion 430 when closed. A similar retaining member can alternatively or additionally be hingingly attached to second portion 430. As an alternative to a hinging motion, such retaining member can rotate in a passage or slot formed in carrier 410.

Figure 4I:
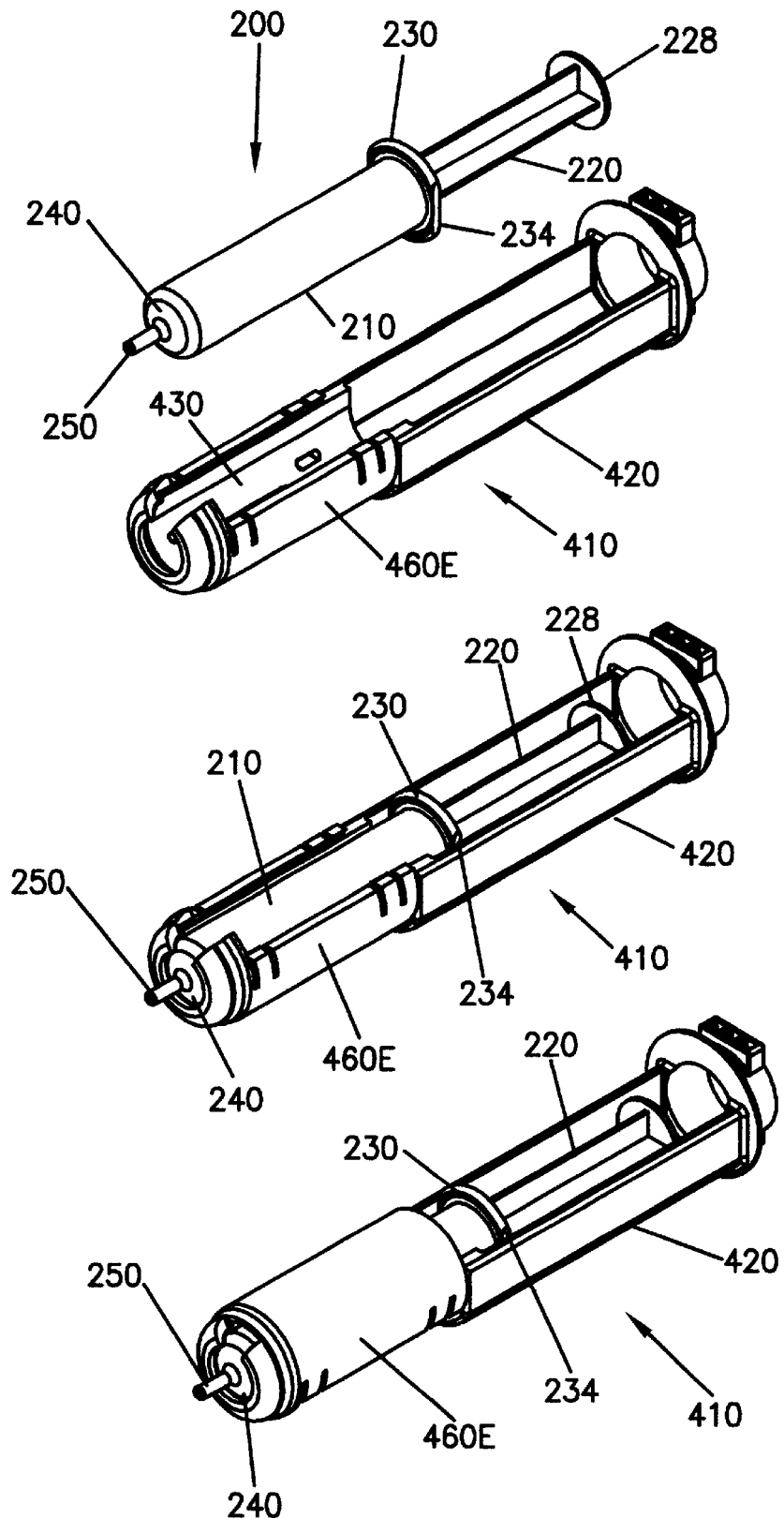
FIG. 4I illustrates a perspective view of an adapter including another embodiment of a syringe retaining member.

An example of a widened, rotating retaining member 460e is illustrated in FIG. 4I. Retaining member 460e is rotatably attached (about the longitudinal axis of carrier 410) to second portion 430 and extends generally along the entire length of second portion 430. After syringe 200 is top loaded into carrier 420, retaining member 460e can be rotated to form a cover over second section 430. Retaining members 460d and 460e can be transparent or formed with cut away sections to enhance the visibility of syringe 200.

Figure 5A:
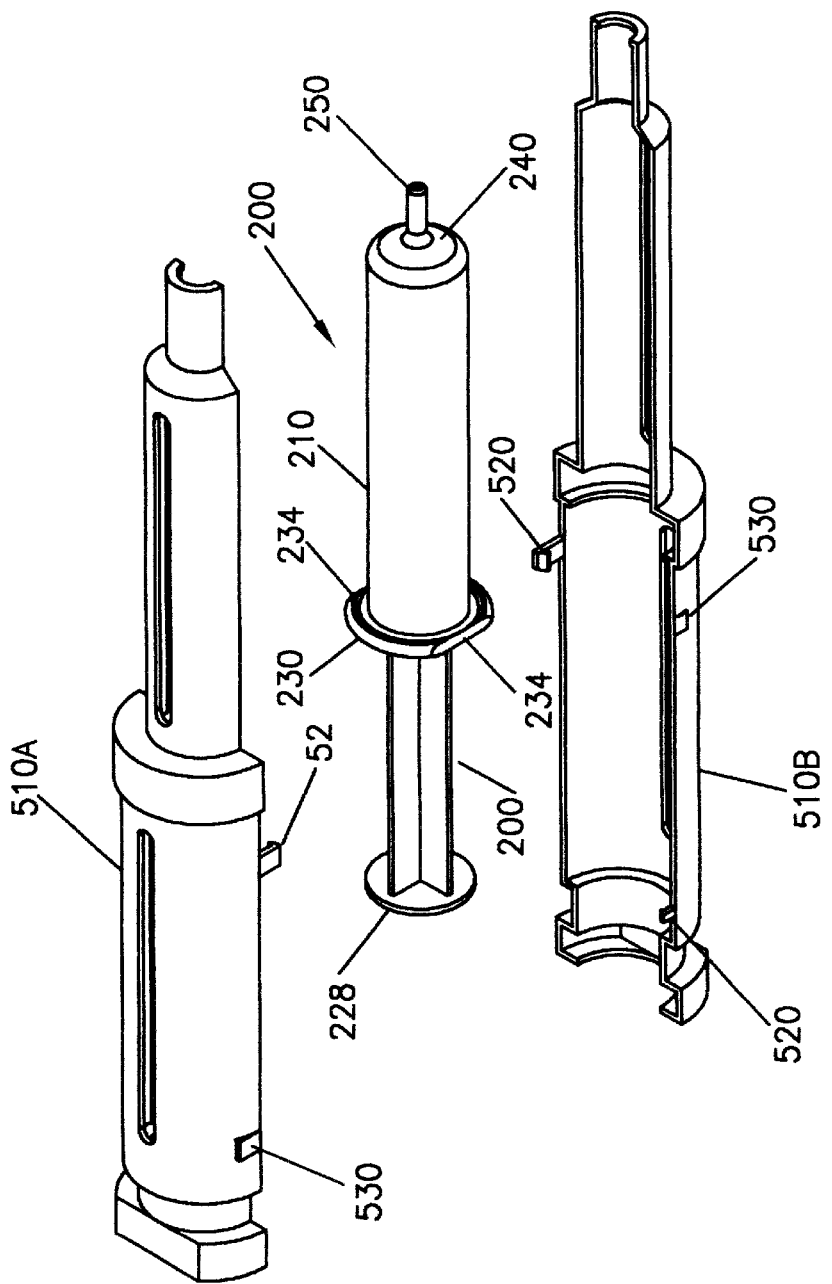
FIG. 5A illustrates a perspective view of an embodiment of an adapter including separate, generally identical sections in an unconnected state.
Figure 5B:
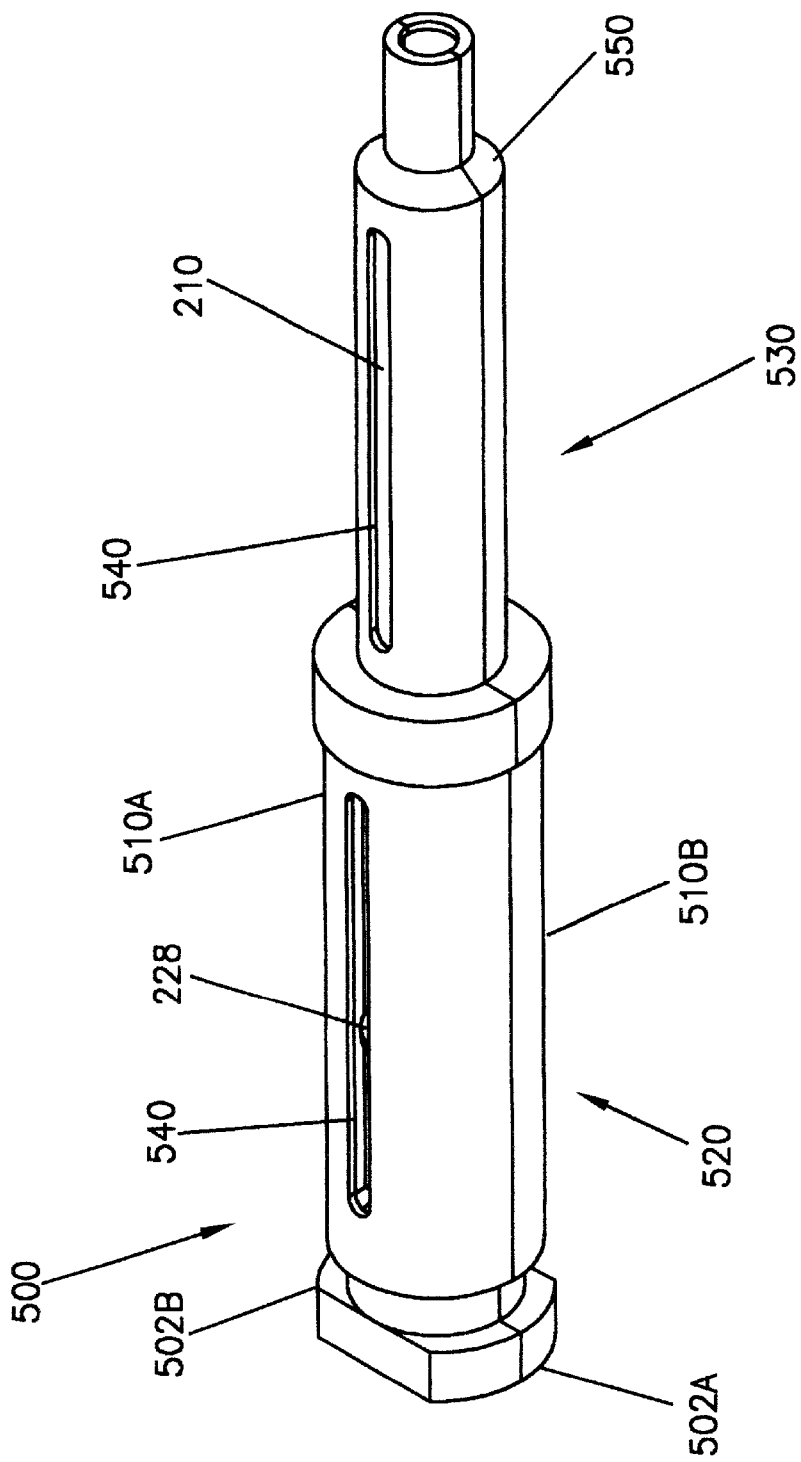
FIG. 5B illustrates a perspective view of the adapter of FIG. 5A in a connected state.

In some cases it may be desirable to manufacture the adapter of the present invention to be disposable after one or more uses. Such disposable adapters are preferably manufactured in an inexpensive manner. In FIGS. 5A and 5B, an embodiment of a preferably disposable adapter 500 is illustrated. Adapter 500 preferably includes two generally identical members 510a and 510b. Fabricating adapter 500 from two generally identical members 510a and 510b may substantially reduce manufacturing costs. Members 510a and 510b may for example be fabricated to "snap" together (for example, via extension members 520 and cooperating catch members 530) and provide visible, audible and/or tactile feedback to indicated proper connection.

In use, syringe 200 is preferably seated in one of members 510a or 510b. The other portion is then, for example, snapped into place to encompass syringe 200 within the resultant adapter 500 (see FIG. 5B). When assembled, portions 510a and 510b form a rearward section that houses plunger extension rod 220 and a forward portion that houses syringe barrel 210. At or near a rearward end of adapter 500, members 510a and 510b preferably form a connecting section including first mounting flange 502a and a second mounting flange 502b adapted to removably attach adapter 500 to injector 10 as described above. As illustrated in FIG. 5b, adapter 500 encompasses both syringe barrel 210 and plunger extension rod 220 to retain/stabilize syringe 200. The side walls of adapter 500 can be formed with a generally flat or flattened profile to interact with/abut generally flat section(s) 234 of syringe flange 230 to prevent rotation of syringe 200 about its axis within adapter 200.

To facilitate viewing of either plunger extension rod 220 or barrel 210, adapter 500 can be formed with cut out window sections 540. Moreover, any portion or all of adapter 500 can be transparent.

Adapter 500 provides resistance to the forward force applied to plunger extension rod 220 by abutment of syringe transition region 240 with a radially inward extending shoulder section 550. The advantages of providing such resistance/retention by abutment of syringe transition region 240 discussed above in connection with other embodiments of adapter of the present invention are also provided by adapter 500.

Figure 6A:
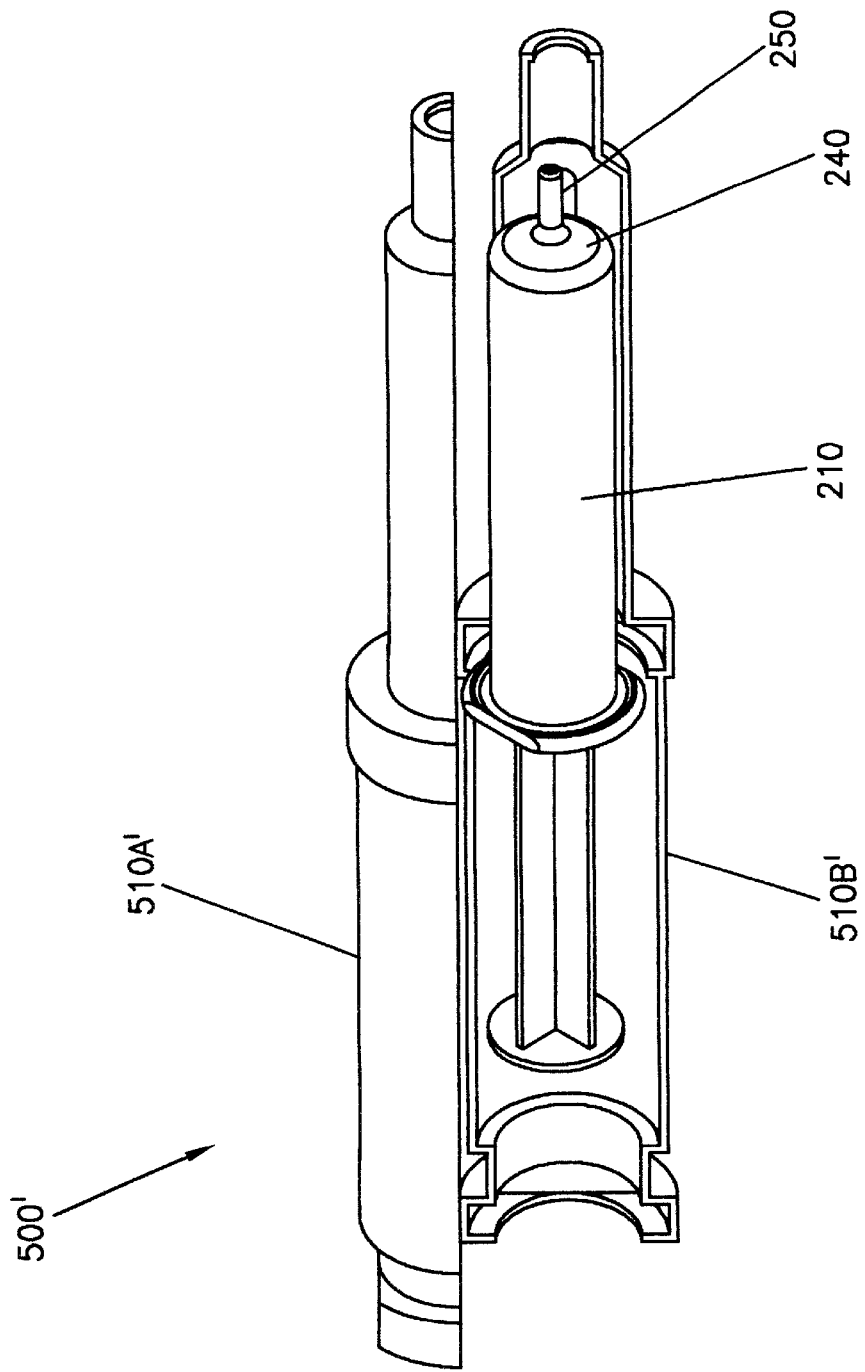
FIG. 6A illustrates a perspective view of another embodiment of an adapter including generally identical sections that are hingingly attached via a side wall thereof.
Figure 6B:
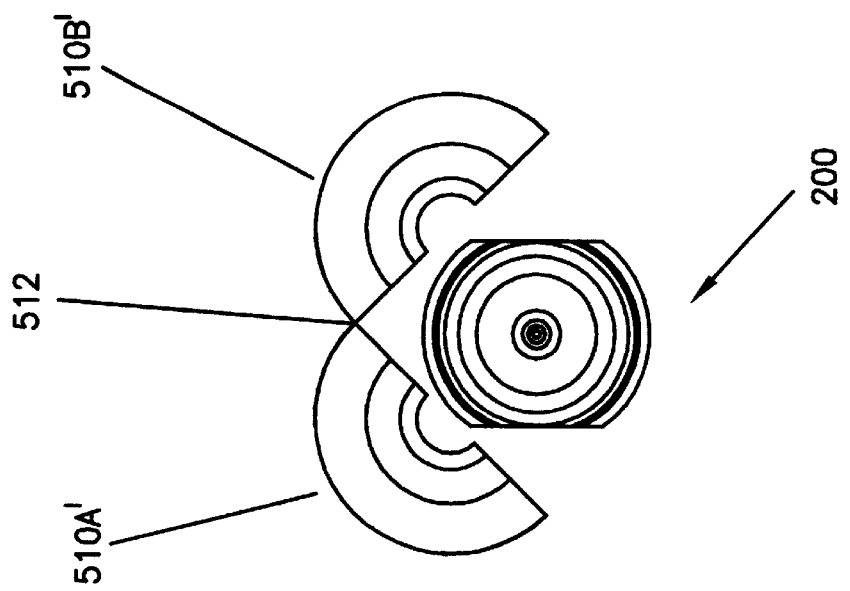
FIG. 6B illustrates a front view of the adapter of FIG. 6A in an open state.
Figure 6C:
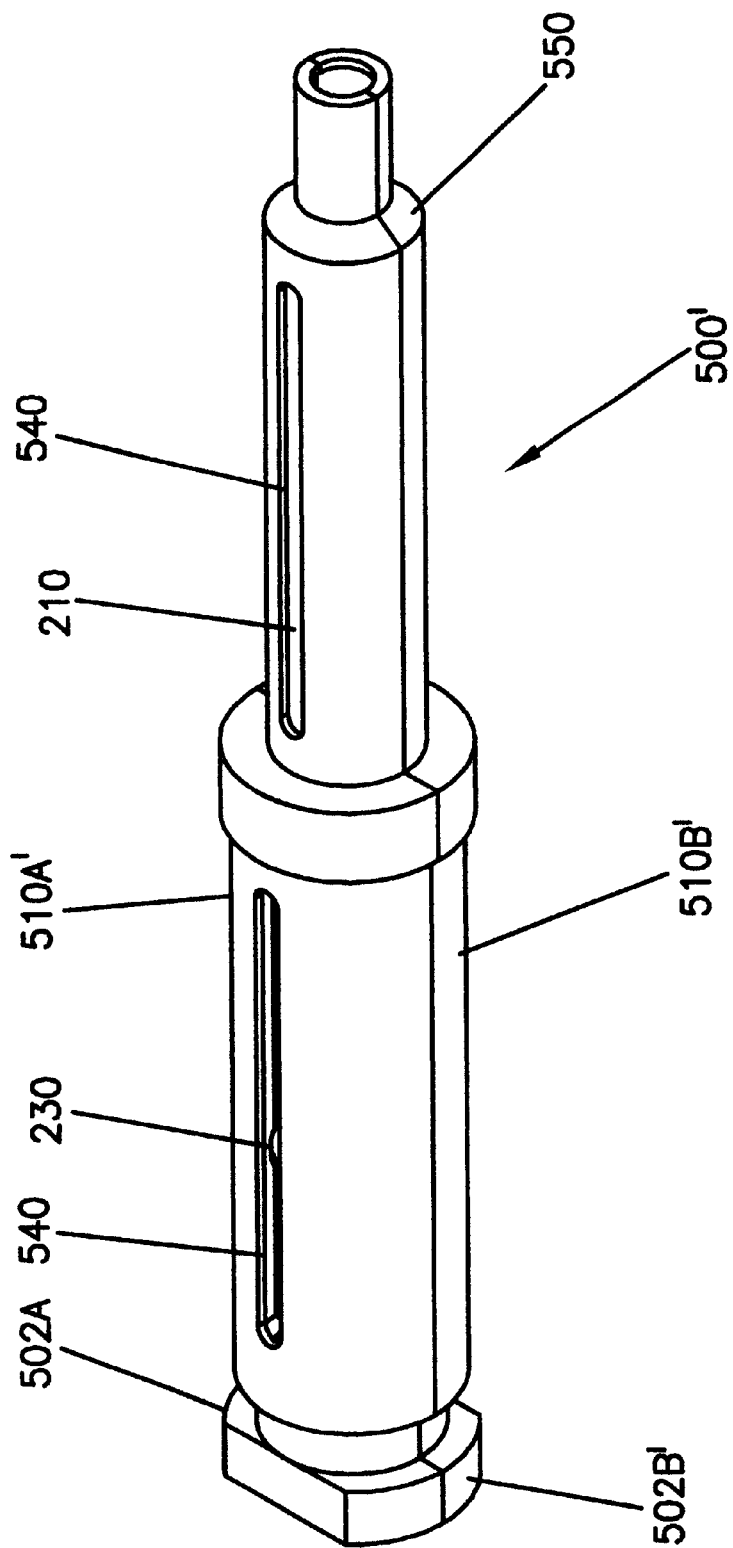
FIG. 6C illustrates a perspective view of the adapter of FIG. 6A in a closed state.

Another embodiment of an adapter 500' is illustrated in FIGS. 6A through 6C. Adapter 500' is generally identical to adapter 500 except that adapter 500' is formed from the connection of a first portion 510a' and a second portion 510b' that are initially hinged together, for example by a notched plastic hinge 512 as known in the art) as best illustrated in FIGS. 6A and 6B.

Figure 7A:
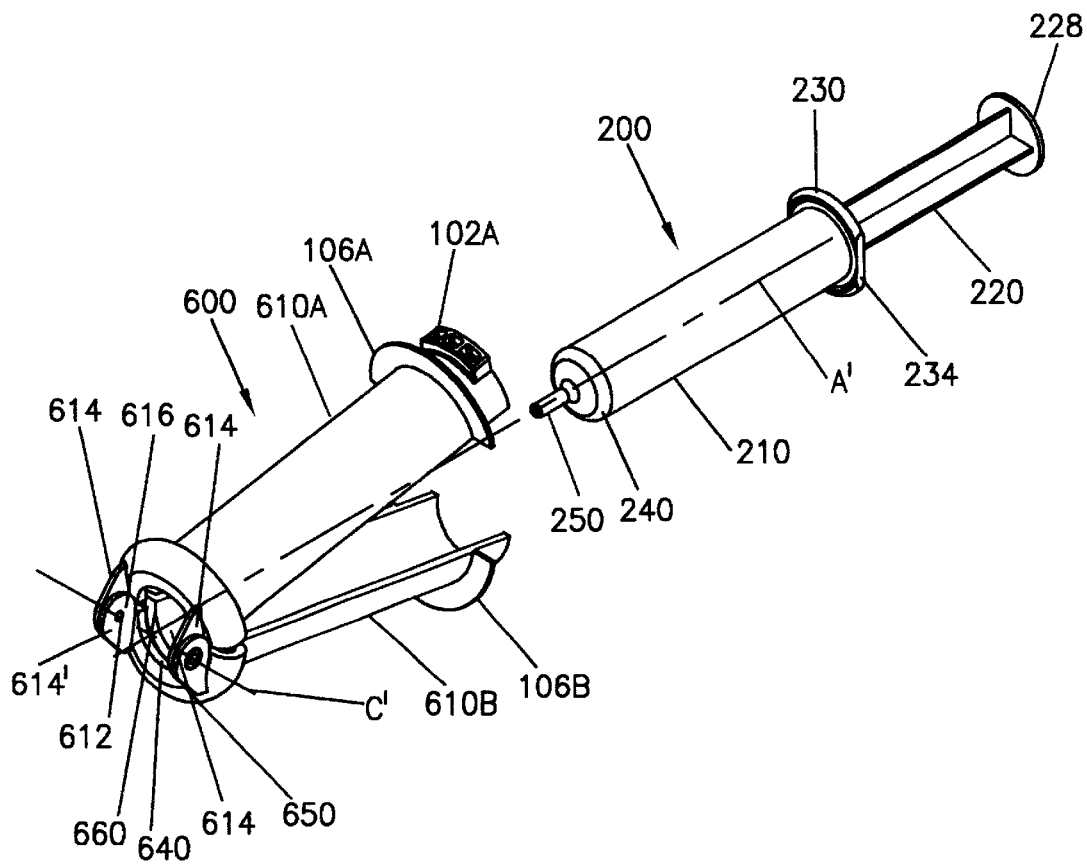
FIG. 7A illustrates a perspective view of another embodiment of an adapter including generally identical sections that are attached at a front end thereof in an open state.
Figure 7B:
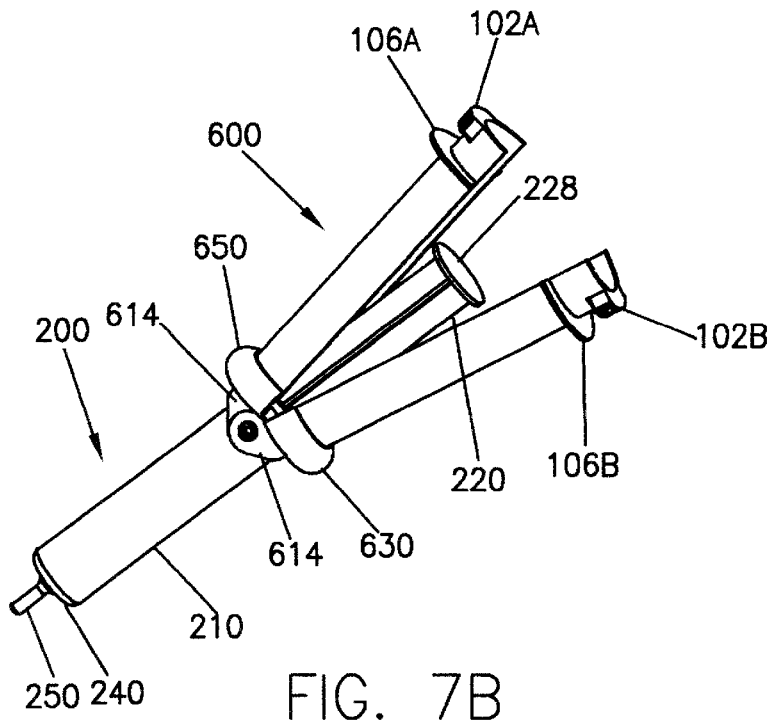
FIG. 7B illustrates the adapter of FIG. 7A with a syringe loaded therein.
Figure 7C:
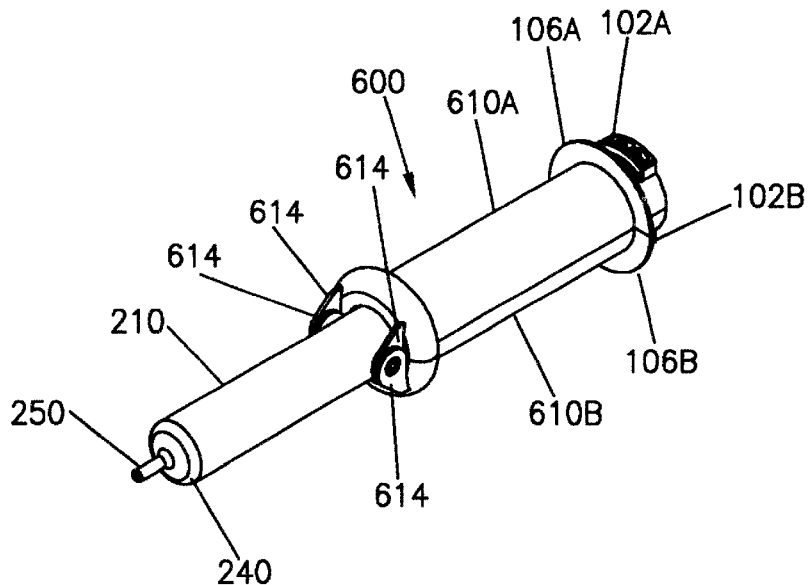
FIG. 7C illustrates the adapter of FIG. 7A wherein the sections thereof have been hingingly closed for connection of the adapter to an injector.

FIGS. 7A through 7C illustrate another embodiment of an adapter 600 of the present invention. Adapter 600 includes a first member 610a and a second member 610b that are attached via a forward hinge mechanism. The hinge mechanism preferably includes a generally cylindrical member 612 on an extending member 614 of one of first member 610a and second member 610b that is rotatably seatable in a passage 616 formed in an extending member of the other of first member 610a and second member 610b. Extending members 614 preferably extend forward on each side of a forward end of each of first member 610a and second member 610b as illustrated in FIG. 7A.

First member 610a includes first retaining flange 102a as described above, while second member 610b includes second retaining flange 102b that operate to connect adapter 600 to injector 10 as described above. First member 610a preferably includes one half of a drip flange 106a, while second member 610b preferably includes the other half of a drip flange 106b.

To seat syringe 200 within adapter 600, first member 610a and second member 610b are preferably rotated about an axis C' of hinging mechanism (which axis is generally perpendicular to the orientation of longitudinal axis A' of adapter 600) to an open position as illustrated in FIGS. 6A and 6B. Barrel 210 of syringe 200 is then passed through an opening 640 formed at the forward end of adapter 600. Syringe 200 is advanced forward through passage 640 until flange 230 abuts radially inward extending shoulder 650 to retain syringe 200 within adapter 600 and provide resistance to forward force exerted upon plunger extension rod 220 by piston 40'. First member 610a and second member 610b are then rotated to a closed position. As discussed above in connection with adapter 100, shoulder 650 may include a raised (rearward extending) abutment ridge 660 to ensure that contact is made with syringe flange 230 near the point where syringe flange 230 is connected to barrel 210. Forward force exerted upon shoulder 650 assists in maintaining adapter 600 in a closed position as illustrated in FIG. 6C.

Like adapters 500 and 500', first member 610a and second member 610b can be formed to be generally identical. Fabrications costs of adapter 600 can thereby be reduced.

Figure 8A:
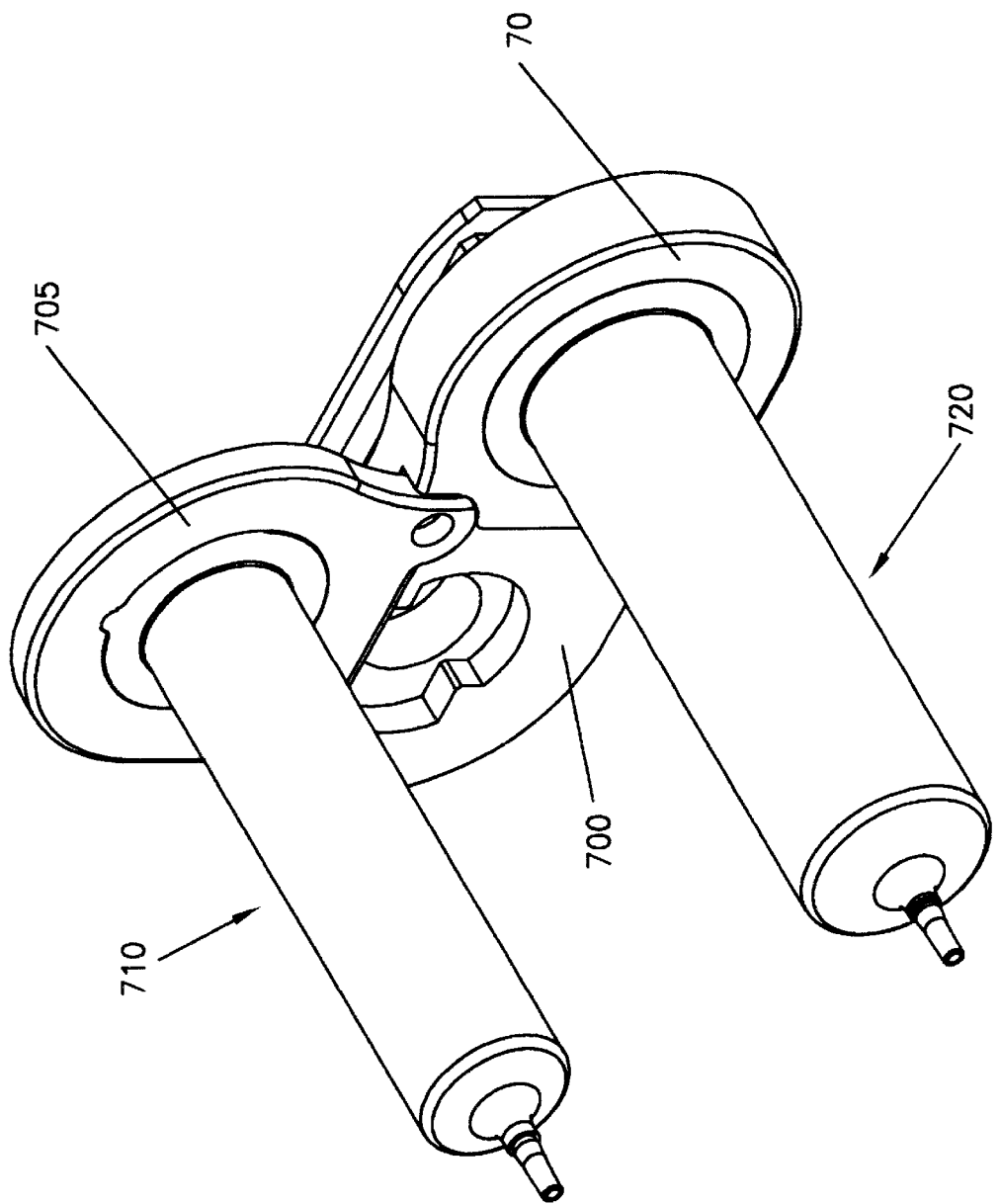
FIG. 8A illustrates a perspective view of a portion of an injector having at least one removable face plate for attachment of a syringe or an adapter thereto.

In all of the embodiment discussed above, the adapter is attached to injector 10 via mounting flanges on a rearward portion or section of the adapter. There are, however, alternative manners in which an adapter of the present invention may be attached to injector 10. As illustrated in FIG. 8A, for example, an injector may include a front wall 700 to which at least one removable face plate 705 is attached. The injector of FIG. 8A is designed for use in an MRI procedure and includes a first, contrast syringe 710 attached to a first face plate 705 and a second, saline syringe 720 attached to a second face plate 705'. In the embodiment of FIG. 8A, face plate 705 is rotated upward to be detached from the injector.

Figure 8B:
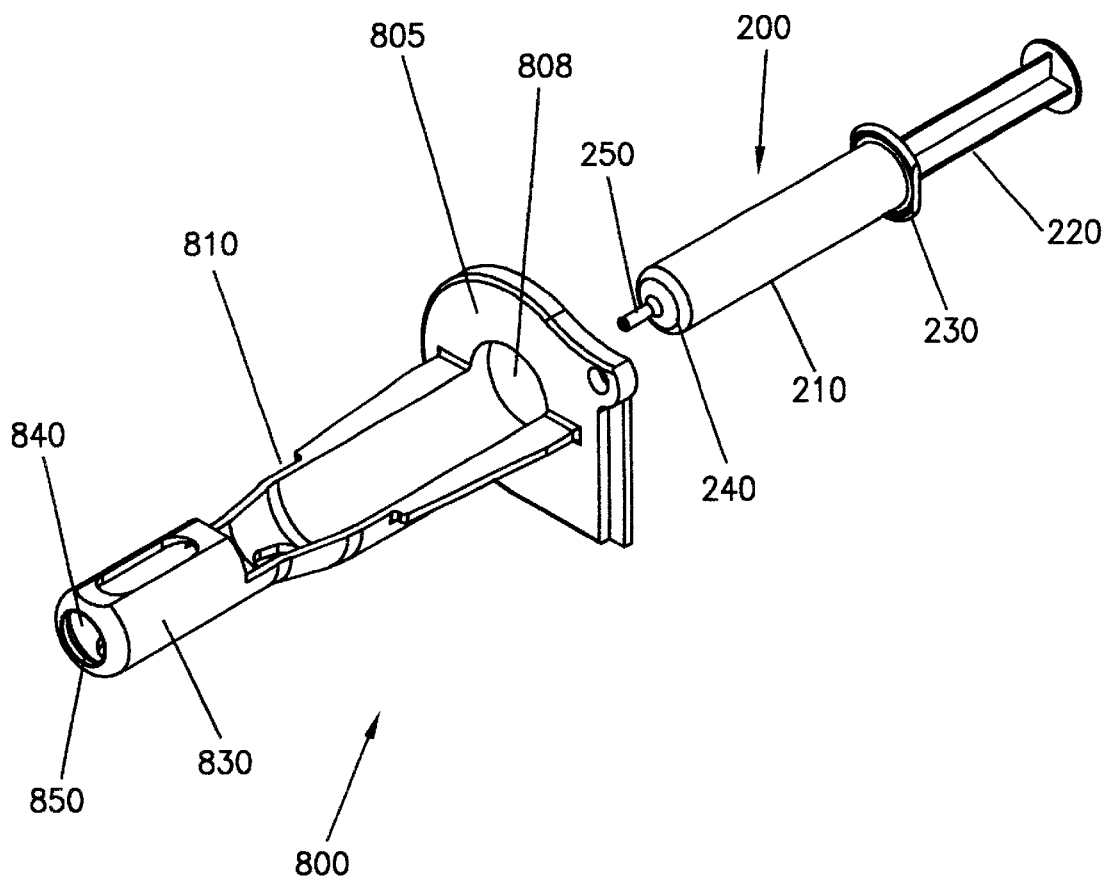
FIG. 8B illustrates a perspective view of an embodiment of an adapter for use with the injector of FIG. 8A.

FIG. 8B illustrates an embodiment of an adapter 800 including a carrier 810 formed integrally or attached to a face plate 805 suitable for attachment to the injector of FIG. 8A. Syringe 200 can be "breach" loaded into carrier 810 by first tilting syringe 200 and advancing barrel 210 of syringe 200 in a forward direction through passage 840 formed in a forward most position of an enclosed forward section 830 of carrier 810. Syringe 200 is advanced until syringe cone region 240 abuts radially inwardly extending shoulder 850 that defines passage 840. Face plate 805 includes a passage 808 therein through which a piston (not shown) of the injector of FIG. 8A can pass to cooperate with plunger extension rod 220.

Figure 8C:
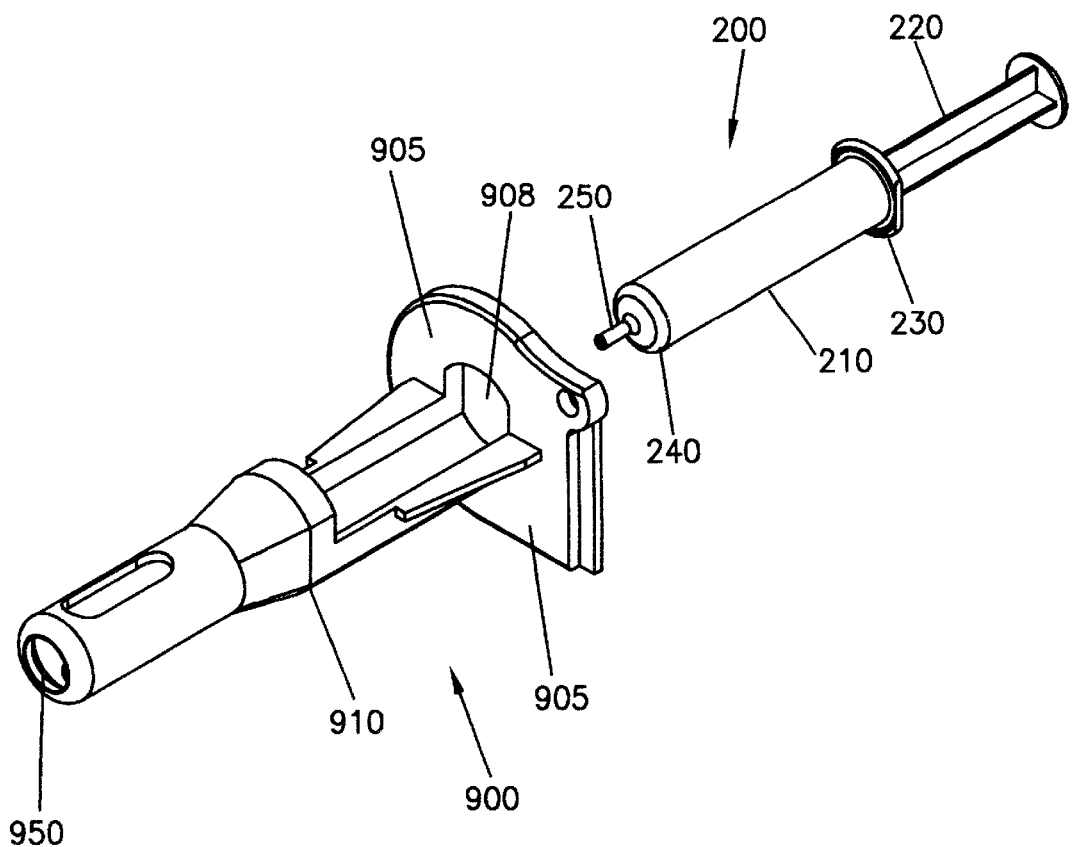
FIG. 8C illustrates a perspective view of another embodiment of an adapter for use with the injector of FIG. 8A.

FIG. 8C illustrates an embodiment of an adapter 900 that includes a carrier 910 attached to a removable face plate 905. In this embodiment, syringe 200 is advanced through passage 908 in face plate 902. Syringe 200 is advanced forward until cone region 240 abuts radially inward extending shoulder 950 of carrier 910.

Figure 8D:
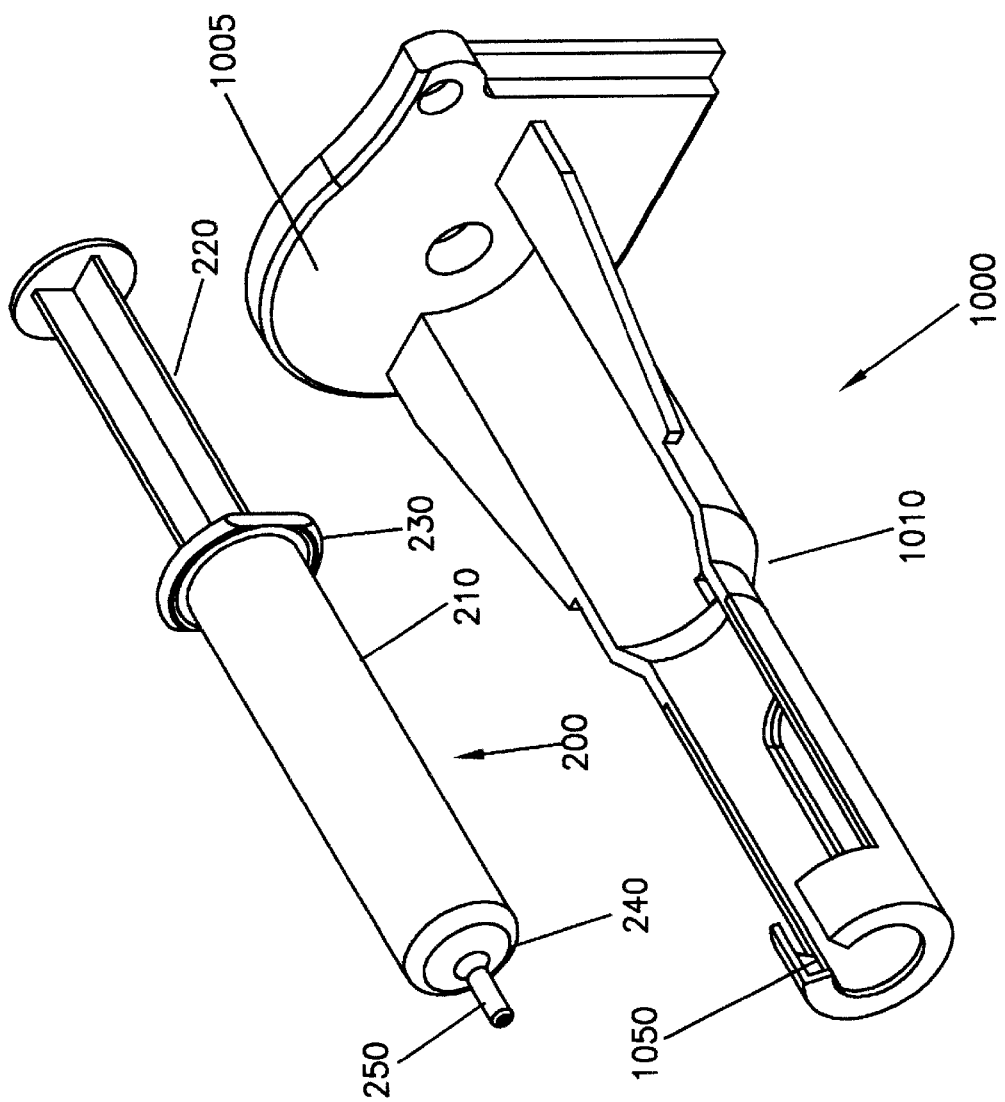
FIG. 8D illustrates a perspective view of another embodiment of an adapter for use with the injector of FIG. 8A.

FIG. 8D illustrates an embodiment of an adapter 1000 that includes a carrier 1010 attached to a removable face plate 1005. Syringe 200 is loaded into carrier 1010 from the top by dropping syringe 200 into carrier 1010. When seated in carrier 1010, syringe 200 abuts radially inward extending shoulder 1050 of carrier 1010. The top of carrier 1010 is maintained in an open state over the length of carrier 1010 to facilitate removal of syringe 200 even when connected to a fluid path element.

Figure 8E:
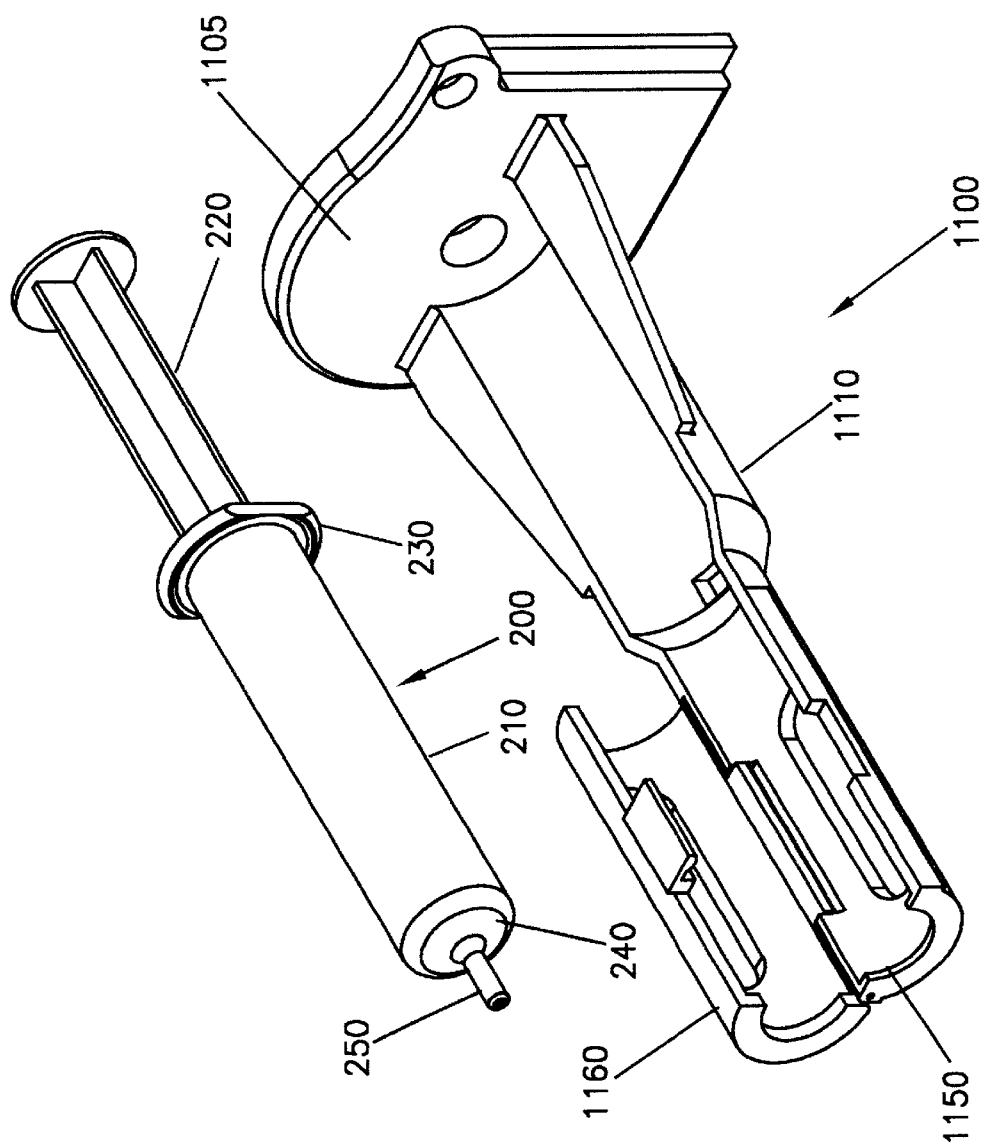
FIG. 8E illustrates a perspective view of another embodiment of an adapter for use with the injector of FIG. 8A.

FIG. 8E illustrates an embodiment of an adapter 1100 that includes a carrier 1110 attached to a removable face plate 1105. Like adapter 1010, syringe 200 is loaded into carrier 1110 from the top by dropping syringe 200 into carrier 1110. When seated in carrier 1110, syringe transition region 240 abuts radially inward extending shoulder 1150 of carrier 1110. Carrier 1110 includes a hinging cover section 1160 that can be rotated to a closed position to form a cover/retainer over at least a portion of syringe barrel 210 to assist in retaining/stabilizing syringe 200. Shoulder 1050 can be rotatable to capture syringe 200 and support it.

Figure 9A:
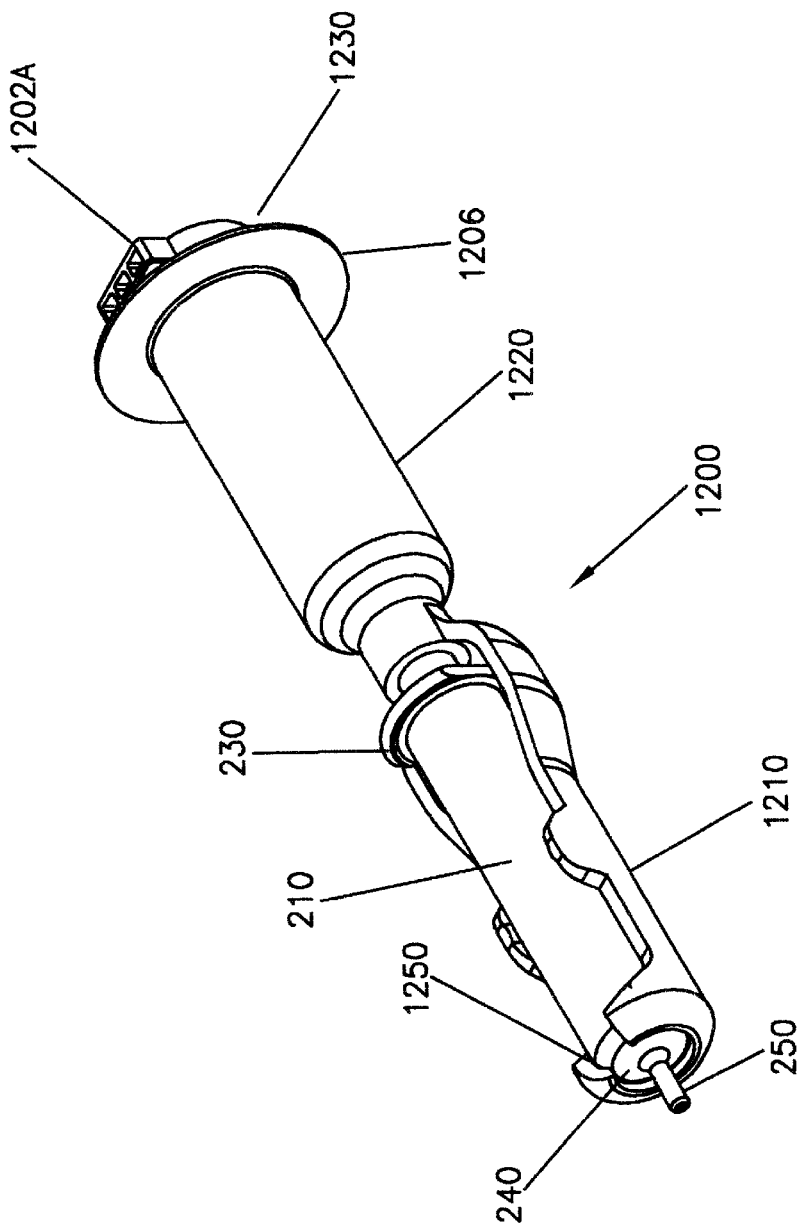
FIG. 9A illustrates a perspective view of an embodiment of an adapter assembly or system in which a push rod performs the function of a syringe plunger extension rod.
Figure 9B:
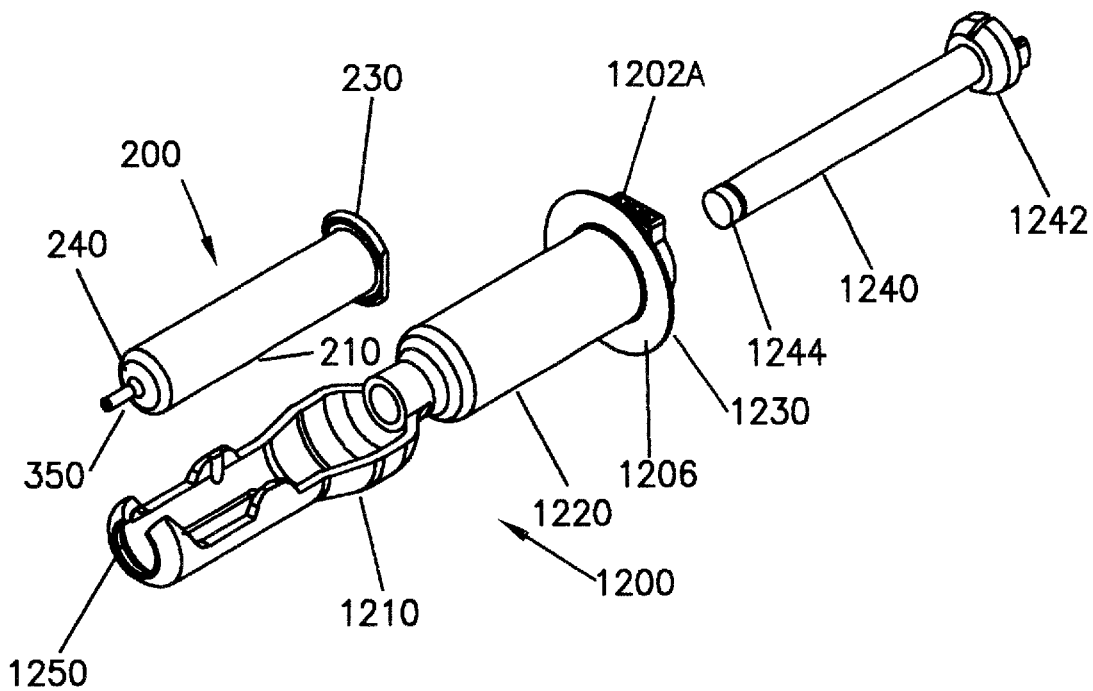
FIG. 9B illustrates a perspective view of the adapter assembly of FIG. 9A in a disconnected state.
Figure 9C:
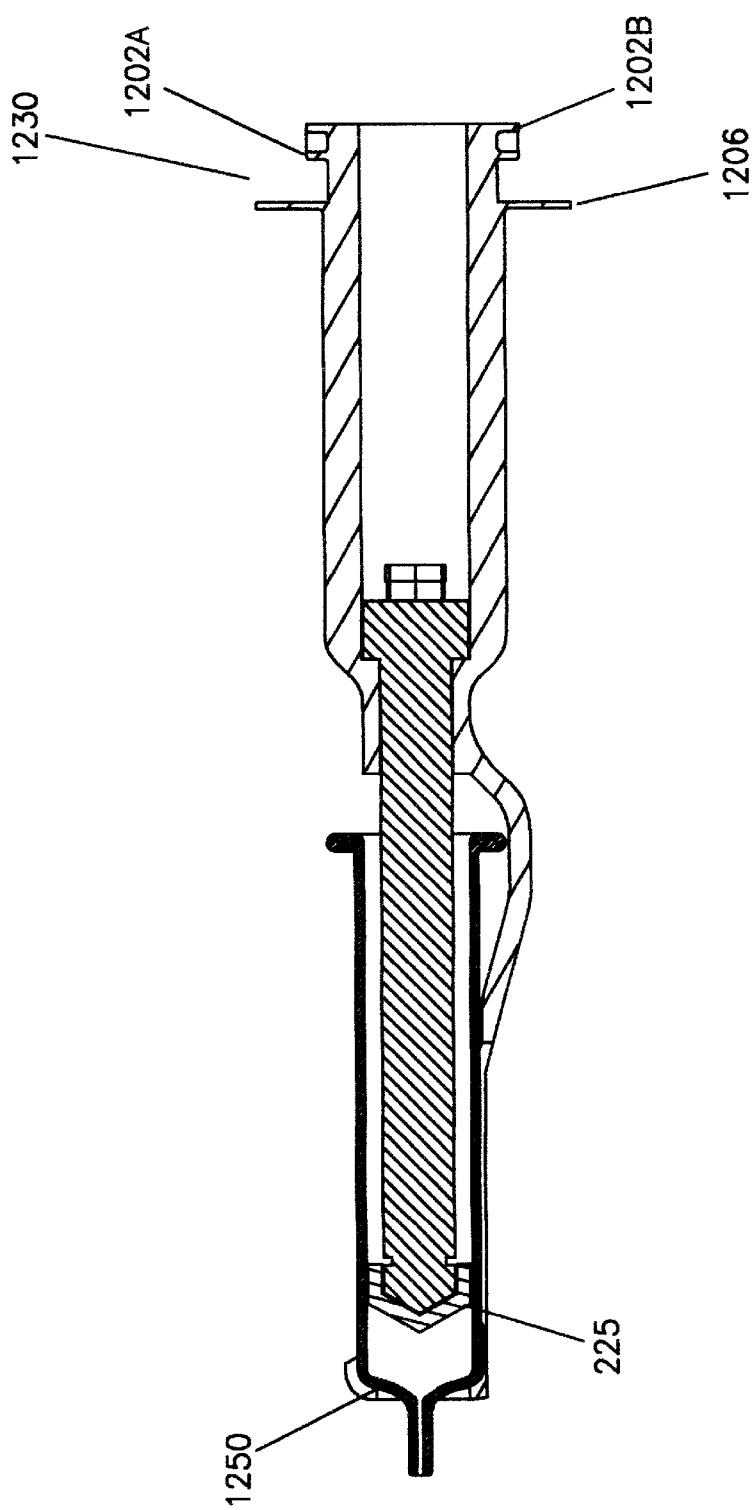
FIG. 9C illustrates a cross-sectional view of the adapter assembly of FIG. 9A.

FIGS. 9A through 9C illustrate an embodiment of an adapter system 1200 including a carrier section 1210, an intermediate section 1220, and a rearwardmost connecting section 1230. Adapter 1200 further includes a push rod 1240. Syringe 200 is seated in carrier section 1210 by dropping syringe 200 into carrier section 1210. Cone region 240 abuts shoulder 1250 of carrier section 1210. The plunger extension rod (not shown) has been removed from connection with syringe plunger 225. In many cases, such plunger extension rods are connected to plunger 225 via threading on the forward end of the plunger extension rod.

Push rod 1240 extends through intermediate section 1220 to cooperate with plunger 225 to apply force to plunger 225. In the case of a prefilled syringe, there is typically no need to retract plunger 225 within syringe 200. In such cases, there is no need to establish an engaging connection (threaded or otherwise) between a forward end of push rod 1240 and plunger 225 to resist the force of and couple plunger 225 to push rod 1240 during a retracting motion of push rod 1240. This greatly simplifies the construction and operation of push rod 1240 and the injector.

In operation of adapter system 1200, push rod 1240 makes a connection with a piston (not shown in FIGS. 9A through 9C; see FIG. 1A) of the injector through a connective coupling 1242 on a rearward end of push rod 1240. Connecting section 1230 is removably attached to the injector via the cooperation of mounting flanged 1202a and 1202b and drip flange 1206 with the injector as described above. Syringe 200 can be top loaded into carriage section 1210 either before or after connection of adapter 1205 to the injector via connecting section 1230. Push rod 1240 is advanced forward through intermediate section 1220 by the injector piston until forward end 1244 pilots into syringe plunger 225 to abut a rearward facing wall section within plunger 225. Once again, no secured connection to resist a rearward motion need be effected between push rod forward end 1244 and plunger 225 in, for example, the case of a prefilled syringe or in any other case that retraction of plunger 225 within syringe 200 will not be required. Push rod forward end 1244 is preferably of generally the shape of the rearward facing interior of plunger 225. In this manner, push rod forward end 1244 provides support to plunger 225 to maintain the shape of plunger 225 during use of syringe 200. In many cases, plunger 225 will be fabricated predominantly from an elastomeric cover material. If the side walls of plunger 225 do not make adequate sealing contact with the interior side wall of syringe barrel 210, leakage of contrast to the rear of plunger 225 can occur during advancement of plunger 225.

Although the present invention has been described in detail in connection with the above examples, it is to be understood that such detail is solely for that purpose and that variations can be made by those skilled in the art without departing from the spirit of the invention except as it may be limited by the following claims.

What is claimed is:

1. An adapter for releasably attaching a syringe to an injector, wherein the syringe comprises a body having a forward end and a rearward end, and a plunger slideably positioned within the body, and wherein the injector comprises a front wall, an opening formed in the front wall, and a drive member reciprocally mounted in the injector, the adapter comprising:

a syringe carrier adapted to seat at least a portion of the syringe, the syringe carrier comprising a front end, a rear end and at least one rearward facing abutment member operable to abut at least a portion of a forward facing surface associated with the syringe, the syringe carrier defining an opening therein to allow the drive member of the injector to engage the plunger;

a releasable mounting mechanism associated with the syringe carrier to mount the adapter in a desired position relative to the front wall of the injector;

at least one syringe retaining mechanism for retaining the syringe within the syringe carrier; and a sealing flange positioned forward of the releasable mounting mechanism to abut the front wall of the injector.

2. The adapter of claim 1 wherein the syringe further comprises a syringe neck associated with the forward end of the body, the syringe neck and the body defining a transition region therebetween, the abutment member operable to abut a forward facing surface of the transition region.

3. The adapter of claim 2 wherein the abutment member abuts the transition region only in the vicinity of the transition from the forward end of the body to the syringe neck.

4. The adapter of claim 1 wherein at least a portion of the adapter is formed to enable viewing of the syringe.

5. The adapter of claim 1 wherein the releasable mounting mechanism comprises one or more flanges that cooperate with the injector to mount the adapter to the injector.

6. The adapter of claim 1, further comprising indicia for providing information to the injector.

7. The adapter of claim 1, further comprising at least one syringe abutment member to prevent the syringe from rotating within the adapter.

8. The adapter of claim 1 wherein the at least one syringe retaining mechanism is rotatable around an axis of the adapter between an open position and a closed position.

9. The adapter of claim 1 wherein the drive member does not connectively engage the plunger.

10. The adapter of claim 1 wherein the releasable mounting mechanism is disposed on the rearward end of the syringe carrier.

11. The adapter of claim 1, further comprising a push rod disposed within the opening in the syringe carrier, the push rod comprising a distal end that is operable to engage the plunger of the syringe and a proximal end that is operable to engage the drive member of the injector.

12. The adapter of claim 1 wherein the at least one syringe retaining mechanism is rotatable around an axis of the adapter between an open position and a closed position.

13. An adapter for releasably attaching a syringe to an injector, wherein the syringe comprises a body having a forward end and a rearward end, and a plunger slideably positioned within the body, and wherein the injector comprises a front wall, an opening formed in the front wall, and a drive member reciprocally mounted in the injector, the adapter comprising:
   a syringe carrier adapted to seat at least a portion of the syringe, the syringe carrier comprising a front end, a rear end and at least one rearward facing abutment member operable to abut at least a portion of a forward facing surface associated with the syringe, the syringe carrier defining an opening therein to allow the drive member of the injector to engage the plunger;
   a releasable mounting mechanism associated with the syringe carrier to mount the adapter in a desired position relative to the front wall of the injector;
   at least one syringe retaining mechanism for retaining the syringe within the syringe carrier; and
   at least one syringe abutment member to prevent the syringe from rotating within the adapter.

14. The adapter of claim 13, further comprising a sealing flange positioned forward of the releasable mounting mechanism to abut the front wall of the injector.

15. The adapter of claim 13 wherein the syringe further comprises a syringe neck associated with the forward end of the body, the syringe neck and the body defining a transition region therebetween, the abutment member operable to abut a forward facing surface of the transition region.

16. The adapter of claim 15 wherein the abutment member abuts the transition region only in the vicinity of the transition from the forward end of the body to the syringe neck.

17. The adapter of claim 13 wherein the releasable mounting mechanism comprises one or more flanges that cooperate with the injector to mount the adapter to the injector.

18. The adapter of claim 13, further comprising indicia for providing information to the injector.

19. The adapter of claim 13 wherein the drive member does not connectively engage the plunger.

20. The adapter of claim 13 wherein the releasable mounting mechanism is disposed on the rearward end of the syringe carrier.

21. The adapter of claim 13, further comprising a push rod disposed within the opening in the syringe carrier, the push rod comprising a distal end that is operable to engage the plunger of the syringe and a proximal end that is operable to engage the drive member of the injector.

22. An adapter for releasably attaching a syringe to an injector, wherein the syringe comprises a body having a forward end and a rearward end, and a plunger slideably positioned within the body, and wherein the injector comprises a from wall, an opening formed in the front wall, and a drive member reciprocally mounted in the injector, the adapter comprising:
   a syringe carrier adapted to seat at least a portion of the syringe, the syringe carrier comprising a front end, a rear end and at least one rearward facing abutment member operable to abut at least a portion of a forward facing surface associated with the syringe, the syringe carrier defining an opening therein to allow the drive member of the injector to engage the plunger;
   a releasable mounting mechanism associated with the syringe carrier to mount the adapter in a desired position relative to the front wall of the injector;
   at least one syringe retaining mechanism for retaining the syringe within the syringe carrier;
   at least one syringe abutment member to prevent the syringe from rotating within the adapter; and
   a sealing flange positioned forward of the releasable mounting mechanism to abut the front wall of the injector.

* * * * *